United States Patent [19]

Hardy et al.

[11] Patent Number: 5,541,081
[45] Date of Patent: Jul. 30, 1996

[54] PROCESS FOR ASSESSING OOCYTE AND EMBRYO QUALITY

[75] Inventors: R. Ian Hardy, Newton Centre; David E. Golan, Brookline; John D. Biggers, Auburndale, all of Mass.

[73] Assignees: President and Fellows of Harvard College, Cambridge; Brigham and Women's Hospital, Inc., Boston, both of Mass.

[21] Appl. No.: 215,524

[22] Filed: Mar. 22, 1994

[51] Int. Cl.$^6$ .............................. C12Q 1/02; C12Q 1/26; G01N 21/76
[52] U.S. Cl. .............................. 435/29; 435/25; 436/172; 436/906
[58] Field of Search .................................. 435/29, 25, 4, 435/968; 436/63, 172, 906

[56] References Cited

U.S. PATENT DOCUMENTS

| | | | |
|---|---|---|---|
| 4,449,535 | 5/1984 | Renault | 128/634 |
| 4,658,817 | 4/1987 | Hardy | 128/303 |
| 4,796,639 | 1/1989 | Snow et al. | 128/719 |
| 4,945,896 | 8/1990 | Gade | 128/20 |
| 5,093,238 | 3/1992 | Yamashoji et al. | 435/29 |

FOREIGN PATENT DOCUMENTS

| | | |
|---|---|---|
| WO87/04247 | 7/1987 | WIPO. |
| WO92/12705 | 8/1992 | WIPO. |

OTHER PUBLICATIONS

Chatot, C. et al., An improved culture medium supports development of random-bred 1-cell mouse embryos in vitro, J. Reprod. Fert. 86:679–688 (1989).
Conaghan, J. et al., Selection Criteria for Human Embryo Transfer: A comparison of pyruvate uptake and morphology, J. of Assisted Repro and Genetics 10:21–30 (1993).
Eagle, H., Nutrition Needs of Mammalian Cells in Tissue Culture, Science 122: 501–504 (1955).
Lawitts, J. and J. Biggers, Culture of Preimplantation Embryos, Methods of Enzymology 225:153–164 (1993).
Van Blerkom, J., Microtubule mediation of cytoplasmic and nuclear maturation during the early stages of resumed meiosis in cultered mouse oocytes, Proc. Natl. Acad. Sci. USA 88: 5031–5035 (1991).
Gardner, D. et al., Assessment of Embryo Metablism and Viability, in Handbook of In Vitro Fertilization, Chapter 10, CRC Press, Boca Raton, FL, 1993, 195–211.
Leese, H. et al., Early Human Embryo Metabolism, BioEssays, V. 15 No. 4, Apr. 1993, 259–264.
Biggers J., et al., Metabolism of the Preimplantation Mammalian Embryo, Advances in Reproductive Phys., 1973 6(6) :1–59.
Butler, J. et al., Assessing the Viability of Preimplantation Embryos in Vitro, Theriogenology, Jan. 1989, 31(1):115–126.

Chance B., et al., Properties and Kinetics of Reduced Pyridine Nucleotide Fluorescence of the Isolated and In Vivo Rat Heart, Biochemische Zeitschrift 341, (1965) 357–377.
Epel, D., A Primary Metabolic Change of Fertilization Interconversion of Pyridine Nucleotides, Biochem and Biophys Research Comm., vol. 17, No. 1, 1964, 62–68.
Esumi, K. et al., NADH Measurements in Adult Rat Myocytes During Simulated Ischemia, Am. Physiol. Soc., 1991, H1743–H1752.
Eng, J. et al., Nicotinamide Adenine Dinucleotide Fluorescence Spectroscopy and Imaging of Isolated Cardiac Myocytes, Biophysical J., vol. 55, Apr. 1989, 621–630.
Balaban, R., Regulation of Oxidative Phosphorylation in the Mammalian Cell, Am. J. Physiol., 1990, 258:C377–C389.
Katz, L. et al., Respiratory Control in the Glucose Perfused Heart: A$^{31}$P NMR and NADH Fluorescence Study, FEBS Letters, vol. 221, No. 2, 1987, 270–276.
Heineman, F. et al., Effects of Afterload and Heart Rate on NAD(P)H Redox State in the Isolated Rabbit Heart, Am. J. Physiol 1993, 264:H433–H440.
Laughlin, M. et al., Pyruvate and Lactate Metabolism in the In Vivo Dog Heart, Am. J. Physiol., 1993, 264:H2068–H2079.
Paul, M. et al., Fertilization-associated Light-scattering Changes in Eggs of the Sea Urchin *Strongylocentrotus purpuratus*, Experimental Cell Research, 1971, 65:281–288.
Whitaker, M. et al., The Relation Between the Increase in Reduced Nicotinamide Nucleotides and the Initiation of DNA Synthesis in Sea Urchin Eggs, Cell, vol. 25, Jul. 1981, 95–103.
Turner, E. et al., The Relationship Between a Novel NAD(P)H Oxidase Activity of Ovoperoxidase and the CN–resistant Respiratory Burst That Followss Fertilization of Sea Urchin Eggs, J. Bio Chem, vol. 260, No. 24, Oct. 25, 1985, 13163–13171.
Kohen E. et al., Quantitative Aspects of Rapid Microfluorometry for the Study of Enzyme Reactions and Transport Mechanisms in Single Living Cells, Fluorescence Techniques in Cell Biology, Springer–Verlag, Berlin, 1972, 207–218.
Kohen E. et al., Rapid Microfluorometry for Biochemisty of the Living Cell in Correlation with Cytomorphology and Transport Phenomena, Fluorescence Techniques in Cell Biology, Springer–Verlag, Berlin, 1972, 219–233.
Kohen E. et al., A Topographic Analysis of Metabolic Pathways in Single Living Cells by Multisite Microfluorometry, Experimental Cell Research, 1979, 119:23–30.
Kohen E. et al., New Metabolic Parameters for the Characterization of Cells, Blood Cells 6, 1980, 753–765.

(List continued on next page.)

*Primary Examiner*—Michael G. Wityshyn
*Assistant Examiner*—Ralph Gitomer
*Attorney, Agent, or Firm*—Wolf, Greenfield & Sacks, P.C.

[57] ABSTRACT

Methods and compositions for assessing the quality of an oocyte or pre-implantation embryo are provided. The methods involve comparing the NADH fluorescence of the oocyte or embryo in a control medium to the NADH fluorescence after the oocyte or embryo has been contacted with an essential nutrient.

20 Claims, 14 Drawing Sheets

OTHER PUBLICATIONS

Plachot, M., Choosing the Right Embryo: The Challenge of the Nineties, J. In Vitro Fertilization and Embryo Transfer, vol. 6, No. 4, 1989, 193–194.

Gott A. et al., Non–invasive Measurement of Pyruvate and Glucose Uptake and Lactate Production by Single Human Preimplantation Embryos, Human Reproduction, vol. 5, No. 1, 1990, 104–108.

Slotte H. et al., ATP and ADP in Human Pre–Embryos, Human Reproduction, vol. 5, No. 3, 1990, 319–322.

Hardy K. et al., Human Preimplantation Development In Vetro is Not Adversely Affected by Biopsy at the 8–Cell Stage, Human Reproduction, vol. 5, No. 6, 1990, 708–714.

Benos D. et al., Energy Requirements of the Developing Mammalian Blastocyst for Active Ion Transport, Biology of Reproduction, 1980, 23:941–947.

Benos D. et al., Energy Metabolism of Preimplantation Mammalian Blastocysts, Am. J. Physiol., 1983, 245:C40–C45.

Benos D. et al., Developmental Aspects of Sodium–dependent Transport Processes of Preimplantation Rabbit Embryos, Soc. Gen. Physiol. Ser., 1985, 39:211–235.

Benos D. et al., Current Topic: Transport Mechanisms in Preimplantation Mammalian Embryos, Placenta, 1990, 11:373–380.

Gardner D. et al., Development of A Non–Invasive Ultramicrofluorometric Method for Measuring Net Uptake of Glutamine by Single Preimplantation Mouse Embryos, Gamete Research, 1989, 24:427–438.

Cummins J. et al., A Formula for Scoring Human Embryo Growth Rates in In Vitro Fertilization: Its Value in Predicting Pregnancy and in Comparison with Visual Estimates of Embryo Quality, J. In Vitro Fertilization and Embryo Transfer, vol. 3, No. 5, 1986, 284–295.

Salmon J. et al., Microspectrofluorometric Approach to the Study of Free/Bound NAD(P)H Ratio as Metabolic Indicator in Various Cell Types, Photochem. Photobiol. V. 36, 1982, 585–593.

Kocera P., Evaluation Of The NAD Redox States . . . Microscopia Acta Supp 4 1980 pp. 283–287.

Leese H. J., Uptake of Pyruvate by Early . . . Human Reproduction vol. 1 #3 1986 pp. 181–182.

Gott A., Non Invasive Measurement Of Pyruvate . . . Human Reproduction vol. 5 #1 1990 pp. 104–108.

Leese H., Early Human Embryo Metabolism Bioessays vol. 15 No. 4 Apr. 1993 pp. 259–264.

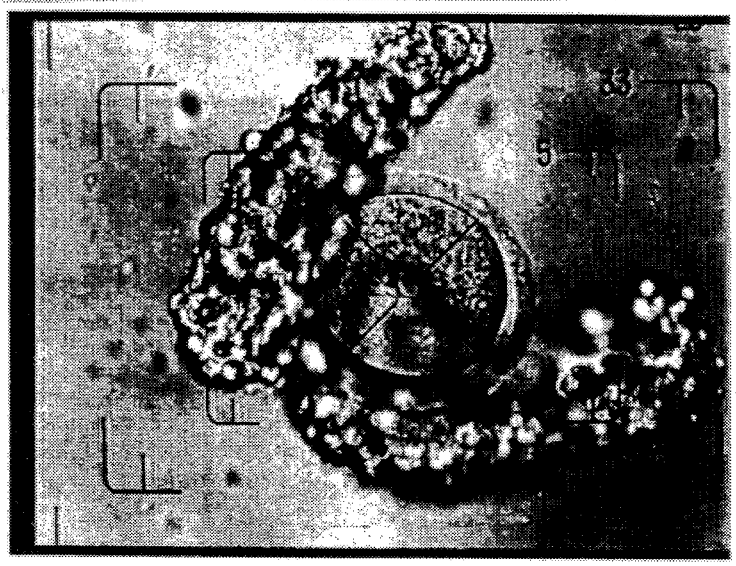
FIG. 2

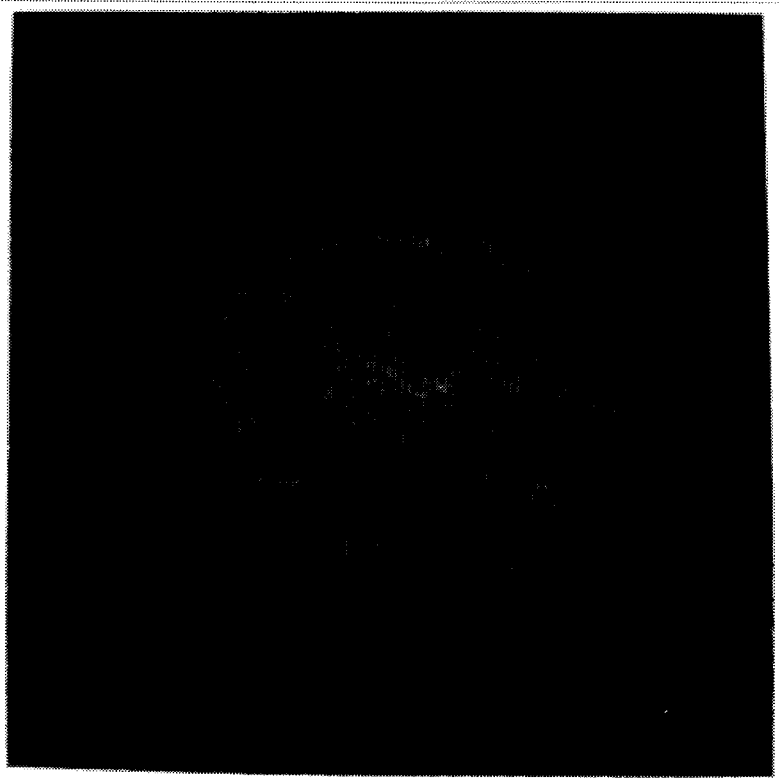
FIG. 8

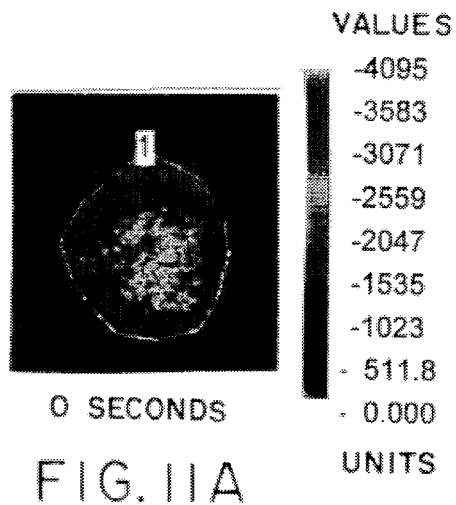
FIG. IIA
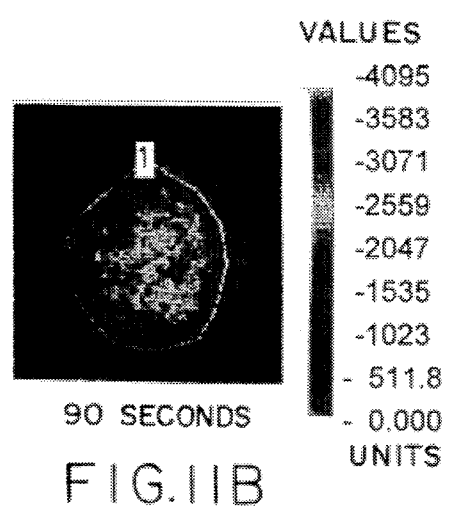
FIG. IIB
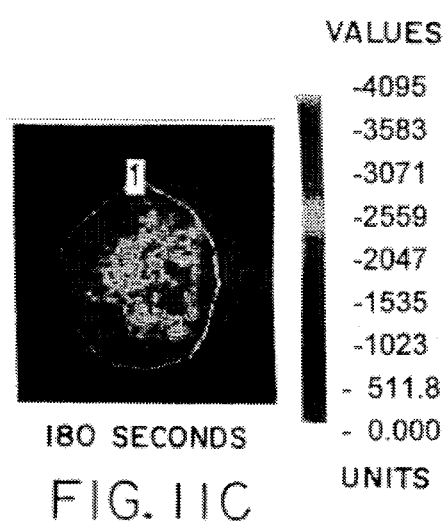
FIG. IIC
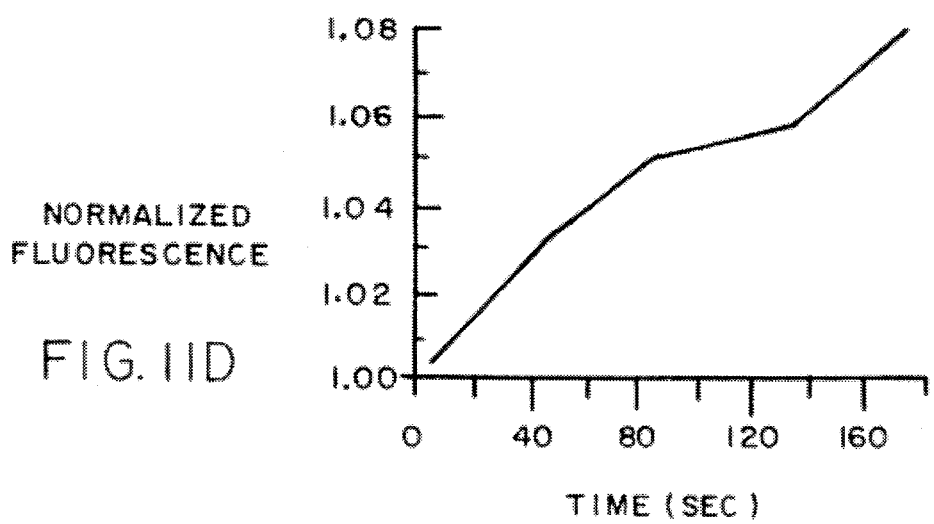
FIG. IID

0 SECONDS

60 SECONDS

120 SECONDS

NORMALIZED FLUORESCENCE

0 SECONDS

60 SECONDS

120 SECONDS

NORMALIZED
FLUORESCENCE

PROCESS FOR ASSESSING OOCYTE AND EMBRYO QUALITY

FIELD OF THE INVENTION

This invention relates to methods and compositions for assessing the quality of an oocyte or pre-implantation embryo. The methods include using a scanning fluorescence microscope photometer or digital imaging fluorescence microscope to measure NADH fluorescence within the oocyte or embryo.

BACKGROUND OF THE INVENTION

The successful transfer of embryos was first reported in 1891 (Heap, W., (1891) Proc. R. Soc. 48, 457–458). Since that time, despite numerous advances in assisted reproductive technologies, the assessment of oocyte and embryo quality has changed very little. Morphologic assessment of oocyte and embryo quality has been recognized as a poor indicator of pregnancy potential (Hardy, R. et al, (1993) Am. Fertility Soc. Annu. Mtg., abstract). Significant improvements in ovulation induction, oocyte retrieval, and in vitro culture techniques have resulted in an abundance of embryos per patient or experimental animal. The embryologist must decide which embryos are the highest quality for transfer, yet lacks the means to objectively define oocyte and embryo quality. Choosing the "right" embryo has been deemed the challenge of the nineties (Plachot, M., (1989) J. IVF-ET 6(4), 193–194).

With the advent of invasive and experimental manipulations of the oocyte and embryo, the need for quality assessment has become increasingly important. Considerable efforts have been invested to determine the potential effects of chorionic villus sampling (Jackson, L. et al, (1992) N. Engl. J. Med. 327(9), 594–598). Despite the advent of pre-implantation cytogenetic diagnosis (Coutelle C. et al, (1989) Brit. Med. J. 299(6690), 22–24), however, the effects of embryo biopsy have been less systematically studied. This is in large part due to the absence of an efficient tool for measuring embryo quality.

The ability to select embryos for uterine transfer or to evaluate the effects of such interventions as pre-implantation embryo biopsy, zona drilling, the use of co-culture techniques, and the experimental use of growth factors or cytokines is markedly limited by current techniques, which utilize morphology or calculated percentages of embryos achieving blastocyst development to assess embryo quality.

Many investigators have recognized the need to develop better techniques to assess oocyte and embryo quality. Proposed methods include a development rating system (Cummins, J. et al, (1986) J. IVF-ET 3(5), 284), fluorescein diacetate fluorescence measurement (Mohr, L. et al, (1980) J. Reprod. Fertil. 58, 189), determination of immunosuppressive activity in pre-implantation culture media (Clark, D. et al, (1989) J. IVF-ET 6(1), 51–58), and measurement of immunoactive factors in culture media including progesterone (Hardy, R. et al, (1993) Soc. Gyn. Invest. Annu. Mtg., abstract), interleukin-1-alpha (Hardy, R. et al, (1993) Am. Fertility Soc. Annu. Mtg., abstract) and interleukin-1-beta (Baranao, R. et al, (1992) Am. Fertility Soc. Annu. Mtg., abstract). All of the proposed techniques have significant limitations, and none is in common use.

The metabolism of pre-implantation embryos has been studied extensively (Biggers, J. et al, (1973) Adv. Reprod. Physiol. 6(0), 1–59; Biggers, J. et al, (1967) Proc. Natl. Acad. Sci. U.S.A. 58(2), 560–567). Renewed interest in the field was prompted by the advent of ultramicrofluorometric technology, which allowed the non-invasive measurement of nutrient uptake (Leese, H. et al, (1984) Anal. Biochem. 140(2), 443–448; Gardner, D. et al, (1986) Hum. Reprod. 1, 25). Glucose and pyruvate uptake, lactate production, and purine utilization have been indirectly quantified using traditional enzymatic analysis based on changes in the concentration of fluorescent NADH in culture media (O'Fallon, J. et al, (1986) Biol. Reprod. 34, 58; Gardner, D. et al, (1987) J. Exp. Zoology 242, 103). The measurement of nutrient uptake has also been carried out in human embryos (Leese, H. et al, (1986) Hum. Reprod. 1, 181; Gott, A. et al, (1990) Hum. Reprod. 5(1), 104–8). It is important to distinguish indirect measurement of NADH in culture media from the direct measurements of NADH within oocytes or embryos. Although an apparatus for measuring the state of oxidation-reduction of a living organ (U.S. Pat. No. 4,449,535, issued to Guy Renault) and more specifically, for monitoring the NADH redox state of brain tissue (WO 92/12705, applicant Mayevsky, A. et al) have been described, there have been no direct measurements of NADH within oocytes or embryos.

Although measurement of nutrient uptake has greatly increased our understanding of embryo metabolism, the general applicability of such analysis is limited because the embryos must be cultured in nanoliter-scale microdrops of media. Current practice for clinical and experimental embryo culture prior to embryo transfer requires a substantially larger volume of culture media; this requirement results in excessive dilution of the NAD(P)H concentration and diminution of measurable NAD(P)H fluorescence in the culture media.

In addition to the problem of measuring nutrient uptake by clinical and experimental oocytes and embryos, the fate of nutrients taken up by the oocyte or embryo (i.e., whether the nutrient in fact enters a productive metabolic pathway within the cell), and the predictive value of the uptake studies with respect to mitochondrial function, have not been established. For example, a recent study reported that pyruvate uptake by human embryos was not predictive of those that successfully implanted (Conaghan, J. et al, (1993) J. Assist. Reprod. Genet. 10(1), 21–30).

In summary, current means for assessing oocyte and embryo viability are inadequate and contribute to the low pregnancy rates of assisted reproduction. At present, on average, only 15% of couples who undergo in vitro fertilization (IVF) procedures have a successful pregnancy outcome. Similar problems exist with large animal transgenic procedures. Invasive manipulations of the oocyte and embryo are currently carried out with unknown consequences to the effect of such manipulations on embryo quality.

SUMMARY OF THE INVENTION

The present invention overcomes these and other problems by providing a high-resolution, non-invasive method for assessing oocyte and embryo quality. Compositions related to this method are also provided. The methods include using a scanning fluorescence microscope photometer or digital imaging fluorescence microscope to measure NADH fluorescence within the oocyte or embryo, and correlating these measurements with successful blastocyst development and pregnancy outcome.

According to one aspect of the invention, a method for assessing the quality of an oocyte or of a pre-implantation embryo (the alternatives referred to hereinafter as "oocyte/ embryo") is provided. The method involves reducing the endogenous NADH concentration of the oocyte/embryo by placing the oocyte/embryo in a control medium (defined below) and obtaining at least one control NADH fluorescence measurement for the nutrient-deprived oocyte/embryo. Thereafter, the oocyte/embryo is contacted with a nutrient for a period of time sufficient for the oocyte/embryo to acquire (i.e., take up and metabolically process) the nutrient. At least one post-nutrient NADH fluorescence measurement is obtained. The quality of the oocyte/embryo is assessed by comparing the control NADH fluorescence measurement(s) to the post-nutrient NADH fluorescence measurement(s). Higher quality oocytes/embryos are those for which the post-nutrient NADH fluorescence measurement is significantly (i.e., at least 2%) greater than the control NADH fluorescence measurement. The method is useful for selecting metabolically healthy embryos for implantation. The above-described methods are also useful for assessing nutrient utilization by the oocyte/embryo and for predicting successful blastocyst development and pregnancy outcome.

According to another aspect of the invention, a simple, non-invasive method for evaluating membrane integrity and function (and obtaining metabolite transfer rates) is provided. The method involves measuring the time of onset of NADH fluorescence increase following nutrient perfusion.

According to another aspect of the invention, a non-invasive method for assessing the progression of oocyte cytoplasmic maturation is provided. Assessment of oocyte cytoplasmic maturation is performed by observing the spatial distribution of NADH fluorescence (indicative of mitochondrial translocation) in the oocyte.

According to still another aspect of the invention, compositions useful for assessing the quality of an oocyte or pre-implantation embryo are provided. The compositions include the oocyte or embryo and a modified control medium. The modified control medium refers to a control medium to which has been added some but not all of the essential nutrients required to support normal metabolic activity. For example, the essential nutrient that is added can be a substrate which participates in the tricarboxylic acid ("TCA") cycle or a precursor to a substrate which participates in the TCA cycle.

The methods for assessing embryo quality are useful for predicting which embryos have the greatest potential for implantation in order to: (i) increase pregnancy rates with assisted reproductive technologies; (ii) increase the number of embryos available for cryopreservation; and (iii) increase the efficiency of offspring from transgenic intervention. The methods for assessing embryo quality are also useful for assessing the impact or effect of current invasive procedures on the oocyte and embryo, including: (i) intracytoplasmic sperm injection; (ii) blastomere biopsy for pre-implantation cytogenetic diagnosis; and (iii) use of co-culture techniques with growth factors, cytokines, and nutrients.

The methods for assessing the progression of oocyte cytoplasmic maturation are useful for assessing whether the appropriate mitochondrial translocation associated with normal oocyte maturity has occurred. The methods for assessing nutrient uptake and transfer times across mitochondrial and plasma membranes, are useful for assessing membrane integrity and hence, cell viability.

These and other aspects of the invention, as well as various advantages and utilities, will be more apparent with reference to the detailed description of the preferred embodiments and to the accompanying drawings.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIGS. 1A and 1B show the frontal and diagrammatical use, respectively. FIG. 1A further shows the following structural limitations of a preferred embodiment: (i) the cover slip must come before the surface indicated at 2; (ii) the maximum height at 4 is 1.500 inches; and (iii) 6 refers to a 0.25 inch aluminum plate that can be dropped into an existing motion frame. FIG. 1B further shows the dimensional requirements of the preferred embodiment of FIG. 1A.

FIG. 2 shows the phase contrast (top) and pseudocolor fluorescence (bottom) images of a germinal vesicle stage mouse oocyte with partially detached cumulus complex, wherein the unique shape of the oocyte-cumulus complex is represented in both the phase contrast image and the pseudocolor image of measured NADH fluorescence. The color values ranging from 255 to 4095 indicate the fluorescence intensity. An increase in fluorescence intensity is reflected by a change in the observed color of fluorescence from violet to blue to green to yellow to orange to red at the highest color value.

FIG. 8 shows phase contrast (top) and pseudocolor fluorescence (bottom) images of a denuded germinal vesicle mouse oocyte. The distribution of NADH fluorescence is consistent with that previously described for mitochondria. Early aggregation of mitochondria occurs immediately before the perinuclear migration associated with cytoplasmic maturation. (Note that FIG. 8 shows the distribution of fluorescence intensity as areas of blue and green.) The color values ranging from 255 to 4095 indicate the fluorescence intensity. An increase in fluorescence intensity is reflected by a change in the observed color in fluorescence from violet to blue to green to yellow to orange to red at the highest color value.

FIGS. 11A–11D show the progressive increase in measured NADH fluorescence after addition of pyruvate to the nutrient-starved one-cell embryo. Fluorescence values are normalized such that the time zero fluorescence value is 1.00. (Note that FIGS. 11A–11D show an increase in the red area with increasing time.) NADH fluorescence is shown at (A) 0 seconds, (B) 90 seconds, (C) 180 seconds and is graphed as a function of time (D).

DETAILED DESCRIPTION OF THE INVENTION

Figure 1A:
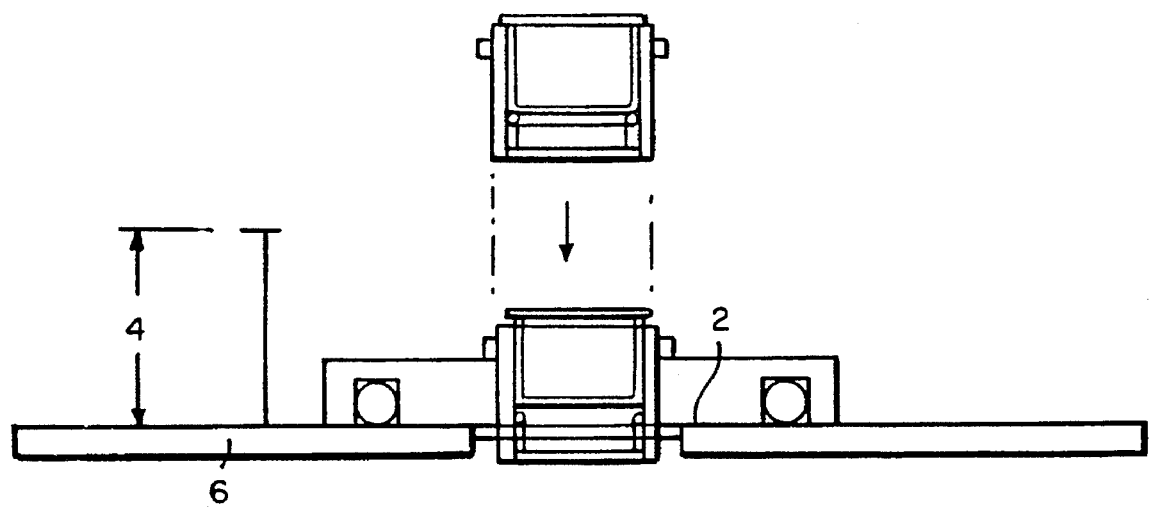
FIGS. 1A and 1B shows the temperature-controlled oocyte/embryo perfusion chamber of the invention.

The invention is useful for assessing the quality of virtually any mammalian oocyte/embryo and can be used, for example, for the purpose of assessing the quality of oocytes/embryos that are intended for implantation into a human recipient, as well as for assessing the quality of oocytes/embryos destined for the creation of transgenic animals or for the preservation of a particular species. The preferred oocytes/embryos include those from the following species: human, mouse, horse, cow, pig and goat.

One method for assessing the quality of an oocyte/embryo that has a steady-state (baseline) concentration of NADH involves: (1) placing the oocyte/embryo in a control medium for a first period of time sufficient to reduce the baseline NADH concentration; (2) obtaining at least one control NADH fluorescence measurement; (3) contacting the oocyte/embryo with a nutrient for a period of time sufficient for the embryo to acquire the nutrient; (4) obtaining at least one post-nutrient NADH fluorescence measurement; and (5) assessing the quality of the oocyte/embryo by comparing the control NADH fluorescence measurement to the post-nutrient NADH fluorescence measurement. The quality of the oocyte/embryo is higher when the post-nutrient NADH fluorescence measurement is significantly greater than the control NADH fluorescence measurement, i.e., the post-nutrient NADH fluorescence measurement is at least 2% greater than the control NADH fluorescence measurement.

In a particularly preferred embodiment, one control NADH fluorescence measurement and one post-nutrient NADH fluorescence measurement are obtained at pre-selected times (the "control pre-selected time" and the "post-nutrient pre-selected time"). The quality of the oocyte/embryo is deemed to be higher when the post-nutrient NADH fluorescence measurement is significantly (i.e., greater than or equal to 2%) higher that the control NADH fluorescence measurement (which is normalized to 1.0).

The "control pre-selected time" refers to a time which is: (i) optimum for reducing the baseline NADH concentration and (ii) relatively constant among oocytes/embryos of the same stage. The "post-nutrient pre-selected time" refers to a time which is: (i) optimum for the oocyte/embryo to take up nutrient and (ii) relatively constant among oocytes/embryos of the same stage. The artisan of ordinary skill in the art can determine the above-described pre-selected times for oocytes/embryos (e.g., n=20) of a particular stage by observing the change in NADH fluorescence as a function of time that the oocyte/embryo is present in the control medium and selecting the time at which the NADH fluorescence is optimally reduced (the control pre-selected time) or the time at which the NADH fluorescence is optimally increased (the post-nutrient pre-selected time).

According to another embodiment, the oocyte/embryo is placed in the control medium for the above-described control pre-selected time, the oocyte/embryo is contacted with nutrient, and at least two post-nutrient NADH fluorescence measurements (an earlier and a later measurement) are made at two different pre-selected times. The quality of the oocyte/embryo is deemed to be higher when the later post-nutrient NADH fluorescence measurement is significantly (i.e., greater than or equal to 2%) higher than the earlier post-nutrient NADH fluorescence measurement.

As used herein, "oocyte" refers to a female germ cell. "Pre-implantation embryo" refers to a fertilized oocyte with two pronuclei (up to and including a blastocyst) but which is not implanted in the lining of the female reproductive tract. In general, in a preferred embodiment, the pre-implantation embryo contains between about 2 and about 8 cells (i.e., the embryo is assessed between about 18 and about 24 hours post-fertilization), although these ranges may vary among species. Typically, the quality assessment for a human or a mouse embryo is performed on an embryo containing between 2 and 8 cells.

The oocyte/embryo contains a steady-state (baseline) concentration of NADH (i.e., the "steady-state NADH concentration") that is present in the cell(s) as a result of metabolic reactions taking place in the mitochondria (e.g., tricarboxylic acid cycle and electron transport) and in the cytosol (e.g., glycolysis). Although one might have expected to find a correlation between metabolic activity and oocyte/embryo viability, past efforts (which involved the indirect measurement of metabolic activity (see the Background)) failed to establish such a correlation. In contrast, the methods disclosed herein (which directly measure oocyte/embryo NADH fluorescence) have been used to establish a correlation between metabolic activity (i.e., the ability to convert energy stored in a nutrient into increased intracellular NADH concentration) and oocyte/embryo viability. (See the Examples and experiments described therein).

To better understand the underlying cellular processes upon which these methods are based, a brief description of one of the key metabolic cycles which produces NADH is provided herein. Living cells possess an intricately regulated system of energy-producing and energy-utilizing chemical reactions. Metabolic reactions that are involved in energy generation break down macromolecules such as carbohydrate, lipid, or protein. Most of the energy-generating metabolic pathways of the cell eventually result in the production of acetyl coenzyme A (acetyl CoA). For example, carbohydrates are metabolized to pyruvate, which is oxidized to acetyl CoA by the pyruvate dehydrogenase system.

Figure 9:
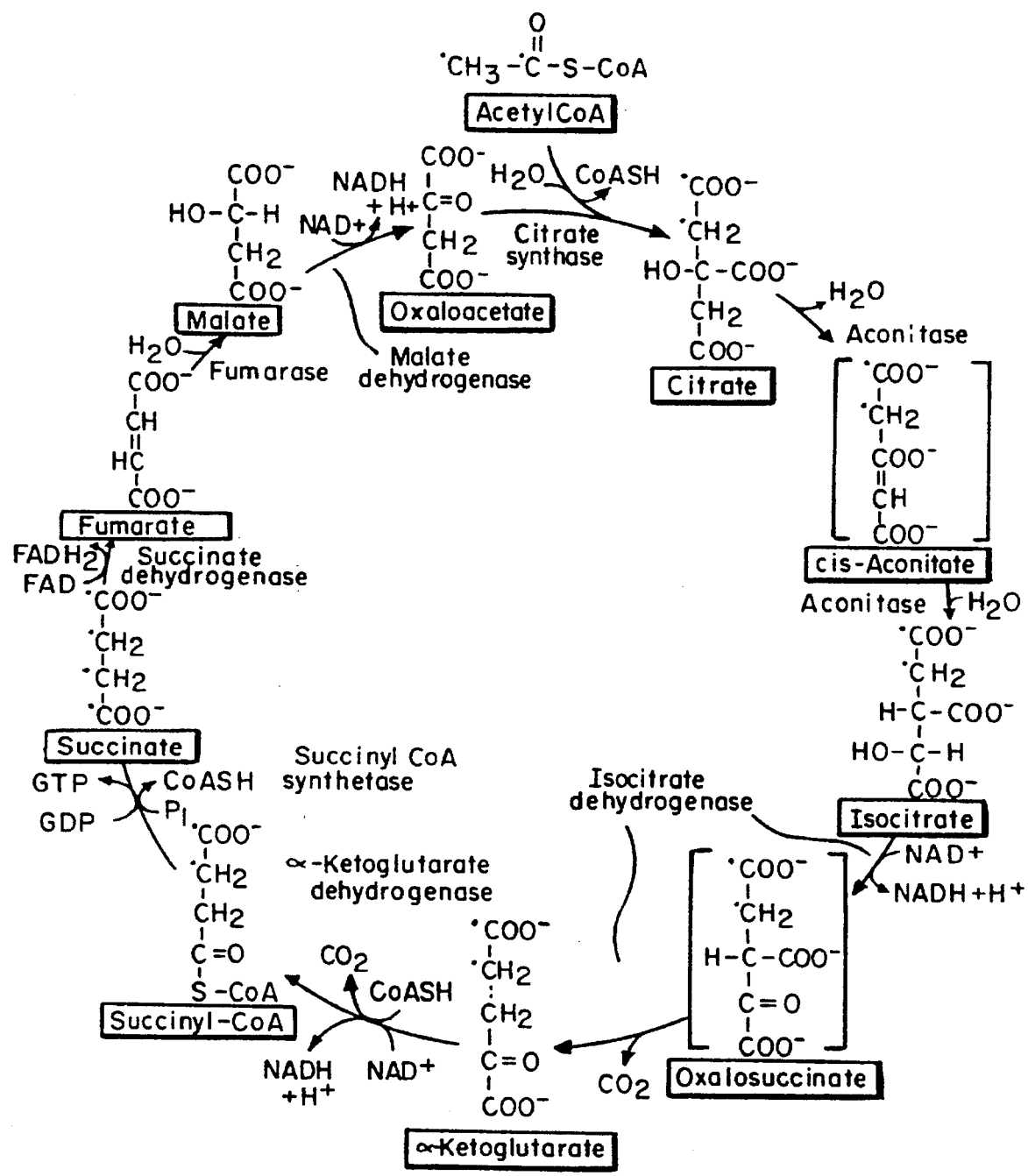
FIG. 9 shows the tricarboxylic acid (Krebs) cycle.
Figure 12A:
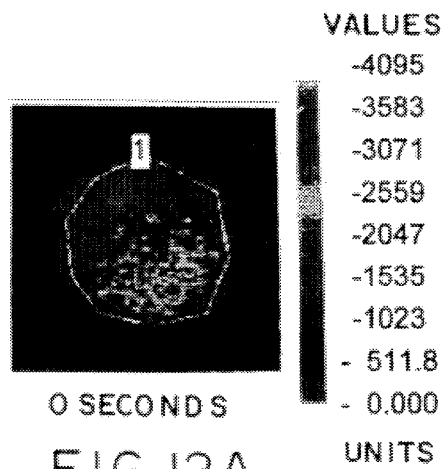
FIGS. 12A–12D show the progressive decrease in measured NADH fluorescence after addition of pyruvate to the nutrient-starved one-cell embryo. Fluorescence values are normalized such that the time zero fluorescence value is 1.00. (Note that FIGS. 12A–12D show a decrease in the red area with increasing time.) NADH fluorescence is shown at (A) 0 seconds, (B) 30 seconds, (C) 60 seconds, and is graphed as a function of time (D).
Figure 12B:
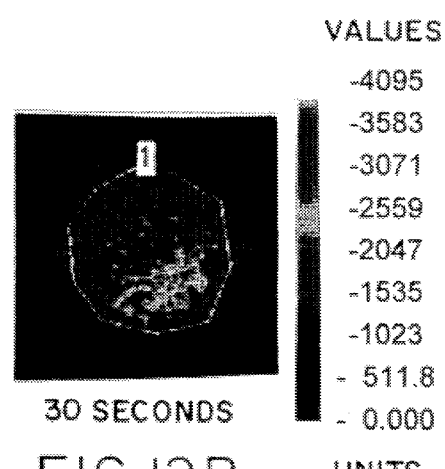
Figure 12C:
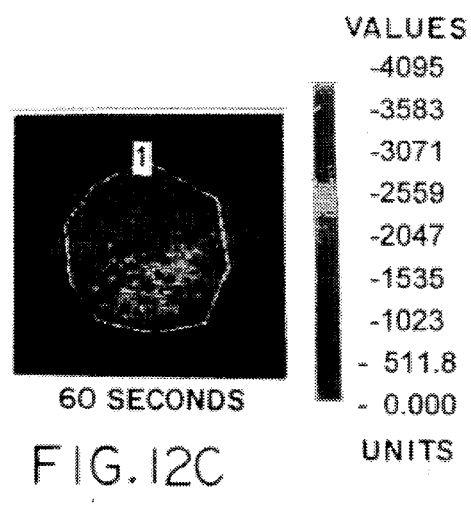
Figure 12D:
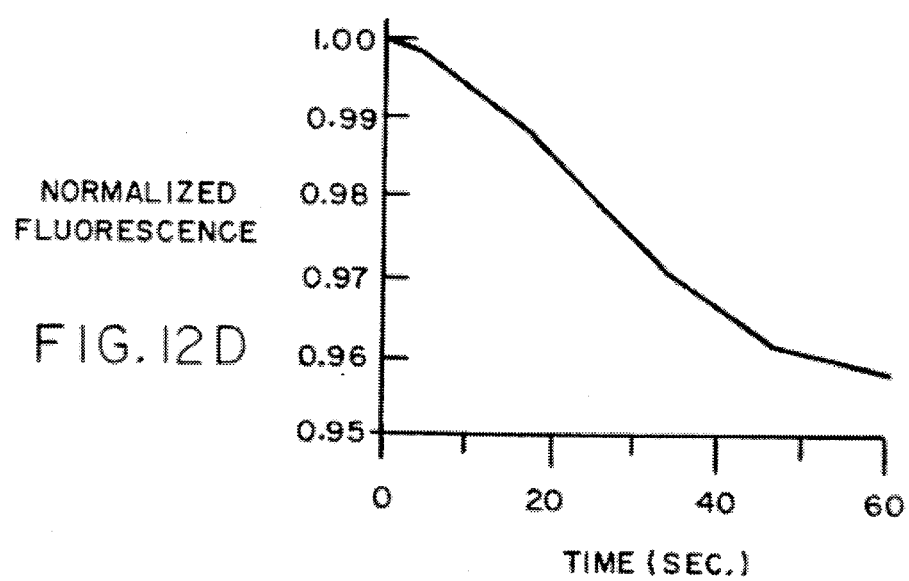
Figure 13A:
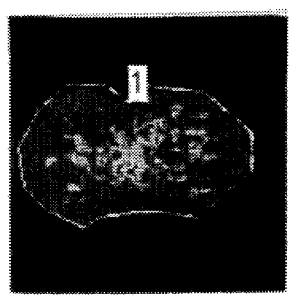
FIGS. 13A–13D show the progressive decrease in measured NADH fluorescence after addition of pyruvate to the nutrient-starved two-cell embryo. Fluorescence values are normalized such that the time zero fluorescence value is 1.00. (Note that FIGS. 13A–13D show a decrease in the red area with increasing time.) NADH fluorescence is shown at (A) 0 seconds, (B) 60 seconds, (C) 120 seconds, and is graphed as a function of time (D).
Figure 13B:
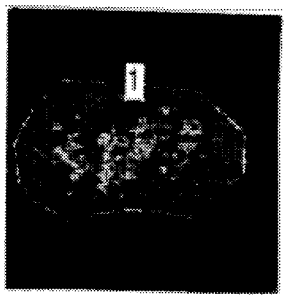
Figure 13C:
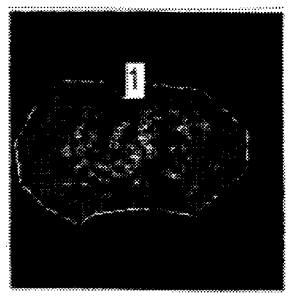
Figure 13D:
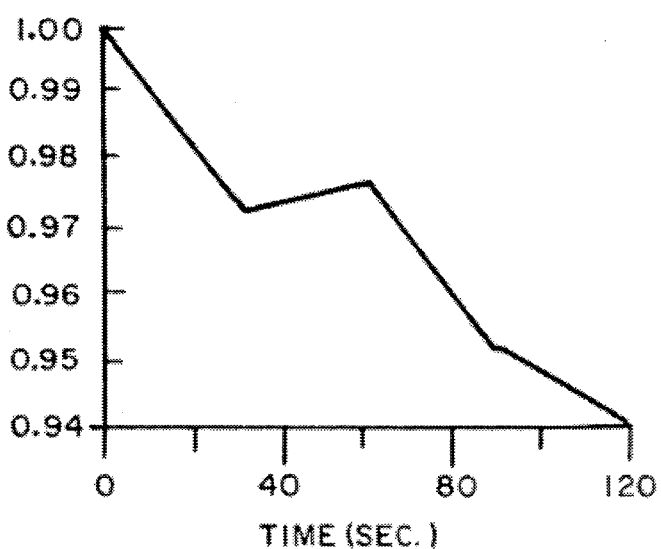
Figure 14A:
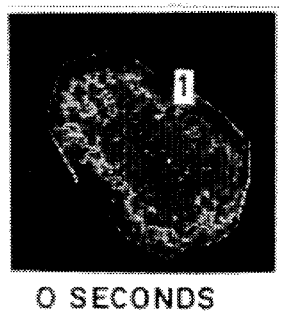
FIGS. 14A–14D show no change in measured NADH fluorescence after addition of pyruvate to the nutrient-starved two-cell embryo. Fluorescence values are normalized such that the time zero fluorescence value is 1.00. (Note that FIGS. 14A–14D show a yellow line encircling an intense red area and that the red area does not change appreciably with increasing time.) NADH fluorescence is shown at (A) 0 seconds, (B) 60 seconds, (C) 120 seconds, and is graphed as a function of time (D).
Figure 14B:
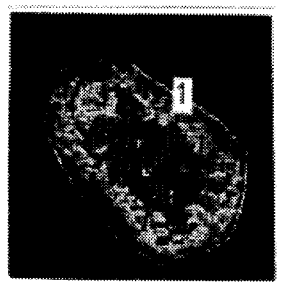
Figure 14C:
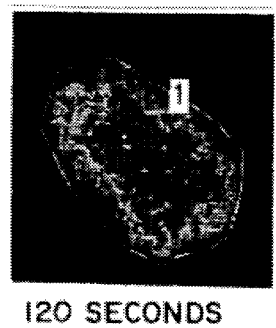
Figure 14D:
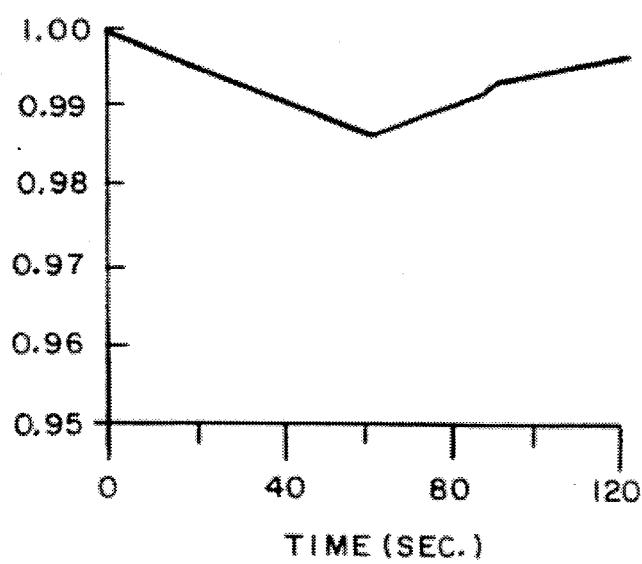

Acetyl CoA is completely oxidized in a cyclic series of oxidative reactions alternately referred to as the tricarboxylic acid (TCA) cycle, the Krebs cycle or the citric acid cycle (FIG. 9). Although certain of the TCA cycle enzymes are also found in the cytosol, where the enzymes function in other metabolic pathways, all of the TCA cycle enzymes are located in the mitochondrion. The oxidation of acetyl CoA in one complete TCA cycle results in the production of two $CO_2$ molecules, one high energy phosphate bond (e.g., such as that present in GTP) and four reducing equivalents (i.e., three NADH and one $FADH_2$ from three NAD+ and one FAD, respectively).

Measuring pyruvate levels in oocyte/embryo culture media as a means of assessing metabolic activity is inadequate for a number of reasons. First, the contribution of pyruvate to the media from cumulus cells surrounding the oocyte cannot be predicted. In addition, the metabolic profile of the oocyte/embryo is complicated by the changing nutrient (e.g., substrate) requirements of the developing embryo from immature oocyte to blastocyst. In the oocyte and early stage embryo, the vast majority of pyruvate that is taken up by the cell is channeled via acetyl CoA into the mitochondrial TCA cycle and oxidative phosphorylation (Wales, R. et al, (1970) Aust. J. Biol. Sci. 23, 877–887). Pyruvate is required to support the first and second cleavage divisions of the mouse embryo in culture (Biggers, J. et al, (1967) Proc. Natl. Acad. Sci. U.S.A. 58(2), 560–567), whereas glucose is unable to support development until the four-cell stage. Glucose is the predominant nutrient required by the blastocyst, however (Brinster, R. et al, (1966) Exp. Cell Res. 42, 303–315). Cells in culture exhibit different nutrient requirements over time. For example, the oxidative metabolism of cultured cells declines over time; such cells become increasingly dependent on anaerobic glycolysis with concomitant lactate production (Morgan, M. et al, (1981) Biosci. Rep. 1, 669–686). Thus, mouse blastocysts which have been cultured in vitro produce almost twice as much lactate as blastocysts which are freshly collected (Gardner, D. et al, (1990) J. Reprod. Fertil. 88, 361–368). Therefore, the simple measurement of pyruvate (nutrient) in culture media cannot be used as a reliable or accurate measure of the mitochondrial or metabolic status of the oocyte/embryo.

In contrast, the present invention provides methods which take into consideration the above-noted unique nutrient requirements and metabolic activities of the developing oocyte/embryo. The methods have been used to delineate the subcellular localization of endogenous NADH fluorescence (Examples 4 and 6), thereby permitting the establishment of a correlation between changes in NADH fluorescence and oocyte/embryo mitochondrial and metabolic activity.

The method for assessing oocyte/embryo quality involves placing the oocyte/embryo in a control medium for a period of time sufficient to reduce the steady state NADH concentration. As used herein, "control medium" refers to a medium which lacks at least one nutrient (e.g., pyruvate, glucose, lactate) that is essential for normal metabolic activity. (See also the Gibco Scientific catalog for a complete listing of essential nutrients and media (including, e.g., Ham's F-10 media, Menezo's B-2 media, CZB media (a non-glucose media) (Table 1)), the entire contents of which are incorporated in their entirety herein by reference). Placing the oocyte/embryo in the control medium perturbs the normal metabolic pathways by which NADH is produced, thereby reducing the steady-state NADH concentration. Exemplary control media include Dulbecco's phosphate buffered saline ("DPBS") and modified CZB media or modified Potassium Simplex Optimization Media ("K-SOM") from which at least one of pyruvate, glucose and lactate is omitted (see Tables 1 and 2).

TABLE 1

| | | CZB MEDIA PREPARATION | | |
|---|---|---|---|---|
| # | COMPOUND | CONC. OF STOCK | GRAMS IN 25 ml | µL in 10 ml |
| 1 | NaCl | 1 M | 2.922 (50 ml) | 820 |
| 2 | KCl | 0.1 M | 0.186 | 486 |
| 3 | $KH_2PO_4$ | 0.1 M | 0.340 | 117 |
| 4 | $MgSO_4$ | 0.1 M | 0.616 | 118 |
| 5 | Na Lactate | 1 M | 4.670* | 301 |

TABLE 1-continued

CZB MEDIA PREPARATION

| # | COMPOUND | CONC. OF STOCK | GRAMS IN 25 ml | μL in 10 ml |
|---|---|---|---|---|
| 6 | Na Pyruvate | 0.1 M | 0.275 | 26 |
| 7 | Glucose | 0.1 M | 0.451 | 0 |
| 8 | Glutamine | 0.1 M | 0.365 | 100 |
| 9 | EDTA (tetra Na salt) | 0.01 M | 0.0095 | 1000 |
| 10 | $NaHCO_3$ | 0.1 M | 0.210 | 2500 |
| 11 | PCN-G | 10,000 U/ML | 0.154 | 100 |
| 12 | Strep | 5 | 0.125 | 100 |
| 13 | BSA | 100 mg/ml | 0.5 in 5 μl | 500 |
| 14 | $CaCl_2.H_2O$ | 0.171 M | 0.628 | 100 |

Table 1 Legend:
*4.670 grams of 60% Syrup
Na lactate, Na pyruvate, $NaHCO_3$, BSA and glucose stocks are made fresh each day of media preparation.
All other stocks are stored at 4 degrees C.
CZB control medium refers to the above-CZB media from which at least one of Na lactate, Na pyruvate and glucose is omitted.

Table 1 Legend:
* 4,670 grams of 60% Syrup
Na lactate, Na pyruvate, $NaHCO_3$, BSA and glucose stocks are made fresh each day of media preparation.
All other stocks are stored at 4 degrees C.
CZB control medium refers to the above-CZB media from which at least one of Na lactate, Na pyruvate and glucose is omitted.

TABLE 2

KSOM MEDIA PREPARATION

| # | COMPOUND | CONC. OF STOCK | GRAMS IN 25 ml | μL in 10 ml |
|---|---|---|---|---|
| 1 | NaCl | 1 M | 2.922 (50 ml) | 950 |
| 2 | KCl | 0.1 M | 0.186 | 250 |
| 3 | $KH_2PO_4$ | 0.1 M | 0.340 | 35 |
| 4 | $MgSO_4$ | 0.1 M | 0.616 | 20 |
| 5 | Na Lactate | 1 M | 4.670* | 100 |
| 6 | Na Pyruvate | 0.1 M | 0.275 | 20 |
| 7 | Glucose | 0.1 M | 0.451 | 20 |
| 8 | Glutamine | 0.1 M | 0.365 | 100 |
| 9 | EDTA (tetra Na salt) | 0.01 M | 0.0095 | 100 |
| 10 | $NaHCO_3$ | 0.1 M | 0.210 | 2500 |
| 11 | PCN-G | 10,000 U/ML | 0.154 | 100 |
| 12 | Strep | 5 | 0.125 | 100 |
| 13 | BSA | 100 mg/ml | 0.5 in 5 μl | 100 |
| 14 | $CaCl_2.H_2O$ | 0.171 M | 0.628 | 100 |

Table 2 Legend:
*4.670 grams of 60% Syrup
Na lactate, Na pyruvate, $NaHCO_3$, BSA and glucose stocks are made fresh each day of media preparation.
All other stocks are stored at 4 degrees C.
KSOM control medium refers to the above-KSOM media from which at least one of Na lactate, Na pyruvate and glucose is omitted.

Table 2 Legend:
* 4,670 grams of 60% Syrup
Na lactate, Na pyruvate, $NaHCO_3$, BSA and glucose stocks are made fresh each day of media preparation.
All other stocks are stored at 4 degrees C.

KSOM control medium refers to the above-KSOM media from which at least one of Na lactate, Na pyruvate and glucose is omitted.

An alternative method for reducing the steady-state NADH concentration in experimental oocytes/embryos involves placing the oocyte/embryo in a medium which contains an inhibitor of a metabolic pathway by which NADH is produced. Exemplary inhibitors of the TCA cycle and a brief description of their sites of action are included in Table 3. The inhibitors are also useful for delineating the subcellular localization of oocyte/embryo NADH fluorescence (see Example 4).

TABLE 3

Summary of metabolic inhibitors and their anticipated effect on intracellular NADH fluorescence

| AGENTS | INHIBITS | ANTICIPATED EFFECT ON NADH | SIGNIFICANCE |
|---|---|---|---|
| Anobarbital | NADH dehydrogenase | Maximally increases | Defines NADH reserve |
| FCCP | Uncouples oxidative phosphorylation | Maximally reduces | Defines NADH = 0 |
| Monofluorocitrate | Aconitase reaction | Reduces | Defines NADH generated from TCA cycle |
| 2-deoxyglucose | Competes with G-6-P (first step in glycolysis) | Slight decrease or no change | befines contribution of glycolysis to NADH generated by a pyruvate perfused oocyte/embryo |
| Iodoacetate | Glyceraldehyde 3-phosphate dehydrogenase (NADH generating step of glycolysis) | Slight decrease or no change | Defines contribution of glycolysis to NADH generated by a pyruvate perfused oocyte/embryo |
| Oxaloacetate | Lactase dehydrogenase | Variable depending on degree of oxidative metabolism | May define ability of cell to continue oxidative metabolism before, during, and after the developmentally regulated shift to glycolysis |

As used herein, "control NADH fluorescence measurement" refers to a measurement of NADH fluorescence that is made at any time during which the oocyte or embryo is present in the control medium. Multiple control NADH fluorescence measurements can be obtained, for example, for the purpose of selecting the amount of time necessary to reduce the steady-state NADH concentration. A photomultiplier tube, photographic film, video camera, or other photon detection device can be used to record the NADH fluorescence image. For example, a photomultiplier tube can be used to measure NADH fluorescence excited by a laser beam at successive locations in a cell (see Examples). Alternatively, a camera can be used to record NADH fluorescence excited by a scanning laser beam or full-field arc lamp illumination. Preferably, the NADH fluorescence image is digitized and stored in a computer for subsequent retrieval and analysis (see Examples). Sources other than an argon laser or an arc lamp that are suitable for illuminating the oocyte/embryo to obtain a fluorescence measurement include, for example, non-argon containing ultraviolet/visible lasers and red and/or near infrared lasers capable of exciting NADH to fluoresce.

In the present embodiment, nutrient was added directly to the oocyte/embryo at time zero, and NADH fluorescence was measured at various time(s) following addition of nutrient. Higher temporal resolution of the rate of change of NADH fluorescence induced by nutrient addition to the oocyte/embryo is optionally achieved by the use of "caged" nutrient compounds in place of nutrient. Caged compounds are photosensitive precursor molecules that generate active effector molecules upon photolysis by laser or flash-lamp illumination. The chemical synthesis and physical properties of caged compounds, laser and flash-lamp photolysis methods, and an outline of some applications of caged compound technology have been recently reviewed (McCray, J. and Trentham, D., (1989) Annu. Rev. Biophys. Biophys. Chem. 18, 239–70). The methods of the present invention are modified to use caged pyruvate, caged glucose, or other caged nutrient compounds as follows. The oocyte/embryo is incubated with control medium to which caged nutrient is added. After a period of time sufficient for the oocyte/embryo to acquire the caged nutrient, photolysis is used to release the active nutrient from its metabolically unavailable caged form. NADH fluorescence is measured at various time(s) following photolytic release of the active nutrient. This modified method permits an extremely accurate measurement of the rate of change of NADH fluorescence induced by nutrient addition to the oocyte/embryo, and obviates the need for oocyte/embryo perfusion by nutrient-containing medium following an incubation period in control medium.

Use of a camera for fluorescence detection with full-field illumination by, e.g., a mercury arc lamp, allows simultaneous recording of fluorescence emission over the entire illuminated area, although the fluorescence signal at each location is weaker than that excited by a laser beam. (See Inoue, S. (1986) Video Microscopy, Plenum Press, New York, 584 pp. for an extended discussion of the range of devices that can be used to record digitized fluorescence emission data and spatial coordinates from samples in a video microscope system.) As recorded and analyzed using any photon detection device, the integrated NADH fluorescence signal over the entire cell can be used as a measure of intracellular NADH concentration. (See also Methods in Cell Biology, (1989) eds. Taylor, K. and Wang, Y., Academic Press, Inc., New York, vol. 29, ch. 14–16 for an extended discussion of fluorescence detection devices.)

In general, the oocyte/embryo is maintained in the control medium for a period of time sufficient to reduce the steady-state NADH concentration. This period of time is determined by monitoring NADH fluorescence as a function of the time of incubation of the oocyte/embryo in the control medium, and selecting the time period required to achieve a decrease in NADH fluorescence. For the mouse oocyte/embryo studies described in Example 2, a thirty minute incubation period in control medium was sufficient to reduce NADH fluorescence. With respect to assessing human oocytes/embryos, the period of time in control medium required to reduce NADH fluorescence is preferably less than thirty minutes, and more preferably, less than about fifteen minutes.

Figure 5:
FIG. 5 shows that NADH fluorescence, excited in a mouse embryo by 351.1–363.8 nm laser light, is detectable at emission wavelengths of 485±22.5 nm (left) but reduced to baseline levels at emission wavelengths of 530±15 nm (right). (Note that FIG. 5 shows areas of blue, green, yellow and red fluorescence intensity at about 485 nm but that no detectable NADH fluorescence (shown as violet) is measured at about 530 nm.) The color values ranging from 255 to 4095 indicate the fluorescence intensity. An increase in fluorescence intensity is reflected by a change in the observed color of fluorescence from violet to blue to green to yellow to orange to red at the highest color value.

The method of the invention utilizes the well known excitation and emission properties of NADH to measure oocyte/embryo NADH fluorescence. The excitation spectrum of NADH has two peaks at approximately 260 nm and 340 nm. The fluorescence emission spectrum of NADH has a maximum at approximately 480 nm and tapers to zero at approximately 530 nm. The specificity of the disclosed method for detecting NADH fluorescence was demonstrated, in part, by illuminating a mouse embryo with ultraviolet (351.1–363.8 nm) light from an argon ion laser and comparing fluorescence emission at 485±22.5 nm (NADH fluorescence) to that at 530±15 nm (no NADH fluorescence). NADH fluorescence was detected at 485 nm (±22.5 nm). At 530 nm (±15 nm), however, the fluorescence was reduced to baseline levels (FIG. 5). The instant invention is not limited in scope to a particular type of filter for detecting NADH fluorescence. Accordingly, other band-pass filters, long-pass filters, or tunable band-pass filters could also be used in accordance with the methods of the instant invention.

The technical feasibility of measuring low-level NADH fluorescence in immature oocytes, mouse embryos (one-, two-, four- and eight-cell embryos) and blastocysts was established using a commercially available interactive laser cytometer (ACAS 570 interactive laser cytometer (Meridian Instruments, Inc., Okemos, Mich.)) (FIGS. 2–4) (see also Example 2). A temperature-controlled oocyte/embryo perfusion chamber (customized for the Meridian ACAS 570 cytometer, see FIG. 1 and Example 1) permitted the continuous measurement of NADH fluorescence during periods of pulsed perfusion with nutrient(s) or metabolic inhibitor(s).

The oocyte/embryo is contacted (e.g., perfused) with the nutrient for a period of time sufficient for the oocyte/embryo to acquire the nutrient. As used herein, "nutrient" refers to a molecule that: (1) is taken up by the oocyte/embryo and (2) is a substrate or cofactor for an enzyme, or a precursor to a substrate or cofactor for an enzyme, which participates in a metabolic reaction or pathway. Exemplary nutrients include pyruvate (a substrate for the pyruvate dehydrogenase enzyme system) and glucose (a substrate used in the glycolytic pathway). Other nutrients include lactate. An exemplary protocol for contacting the oocyte/embryo with a nutrient is provided in Example 2. In a particularly preferred embodiment, pyruvate is the sole nutrient (see Example 4).

In the present embodiment, NADH fluorescence in the oocyte/embryo was excited by ultraviolet (351.1–363.8 nm) light from an argon ion laser. NADH fluorescence can, in principle, be excited by any of several other light sources, with results comparable to or even better than those given in Examples 2, 4, 5 and 6. The only requirement is that the light source must be capable of exciting NADH fluorescence. First, arc lamp illumination (e.g., from a mercury arc lamp) is used. Second, a non-argon containing laser emitting in the ultraviolet and/or visible is used. Third, a laser emitting in the red and/or infrared is used, taking advantage of the recent application of two-photon excitation of fluorescence to laser scanning microscopy (Denk, W. et al, (1990) Science 248, 73–76, and references therein). Two-photon excitation of fluorescence is made possible by the high, spatially localized photon intensity provided by a sharply focused laser at the beam waist, and the temporal concentration of photons provided by a femtosecond to picosecond pulsed laser. In this application, NADH is excited from the ground to the excited state by the simultaneous absorption of two lower energy (higher wavelength) photons rather than one 351.1–363.8 nm photon. Operation of a high power, high frequency laser at red to near infrared wavelengths (about 600–800 nm) excites fluorescence of NADH molecules at the focal plane of the microscope (which is also at or near the plane of the laser beam waist). Use of red to near infrared light to excite NADH fluorescence has several advantages. First, the potential for phototoxicity is minimized because nearly all cellular molecules are transparent at red or near infrared wavelengths. Second, optical sectioning of the oocyte/embryo is facilitated because the two-photon excitation process occurs only at the laser beam waist. Conventional optical sectioning techniques most commonly use confocal scanning laser microscopy and are often associated with photodamage. Optical sectioning by two-photon excitation of fluorescence causes much less photodamage and is used to better define the subcellular localization of NADH fluorescence and to increase the signal to noise ratio of the oocyte/embryo quality assessment assay. Third, in combination with the use of caged nutrient technology, two-photon photolysis is used for fast and localized release of caged nutrient at the subcellular location which is determined to be optimal for performance of the oocyte/embryo quality assay. The utility of two-photon excitation of fluorescence in laser scanning fluorescence microscopy has been demonstrated in several systems using molecules that, like NADH, are excited to fluoresce by near ultraviolet light (Denk, W. et al, (1990) Science 248, 73–76; Szmacinski, H. et al, (1993) Photochem. Photobiol. 58(3), 341–345; Brust-Mascher, I. et al, (1994) Biophys. J. 66(2), A411; Williams R. et al, (1994) Biophys. J. 66(2), A276).

At least one NADH fluorescence measurement (referred to herein as a "post-nutrient NADH fluorescence measurement") is obtained after the oocyte/embryo is contacted with the nutrient. In a particularly preferred embodiment, more than one post-nutrient NADH fluorescence measurement is obtained, and the assessment of oocyte/embryo quality is performed by observing whether successive post-nutrient fluorescence measurements increase with time following nutrient perfusion. The Examples demonstrate that the quality of the embryo is higher (e.g., that the embryo develops successfully to the blastocyst stage) when the successive post-nutrient NADH fluorescence measurements increase as a function of time following nutrient perfusion (see Example 5 and FIG. 15). Successful development to the blastocyst stage is the standard end-point for in vitro embryo assessment and is generally accepted as predictive of embryo quality (see also Example 5 (FIGS. 11–14)).

The rates at which nutrients are transported across cell and mitochondrial membranes are indicative of membrane integrity and function and hence, can also be predictive of cell quality. Increased transfer times have been associated with membrane and cell dysfunction. The rates at which metabolites are transferred across mitochondrial membranes ("transfer rates") have been reported (Kohen, E. et al, (1972) (eds: Thaer, A., Sernetz, M.), Springer-Verlag, Berlin, 207–218; Kohen E. et al, (1979) Exp. Cell Res. 119, 23–30). In contrast to the prior art methods for determining transfer rates, however, the invention provides a simple, non-invasive method for evaluating membrane integrity and function (and obtaining metabolite transfer rates) by measuring the time of onset of the NADH fluorescence increase following nutrient perfusion (see FIG. 7 and Example 5).

The invention also provides a non-invasive, non-toxic method for assessing the progression of cytoplasmic maturation in a test (i.e., sample) oocyte. In general, assessment of oocyte cytoplasmic maturation is performed by: (1) obtaining a first fluorescence measurement showing the spatial distribution of NADH fluorescence at a first time during the early stage of test oocyte meiosis; (2) optionally, obtaining a second fluorescence measurement showing the spatial distribution of NADH fluorescence at a second time during the early stage of test oocyte meiosis; and (3) determining whether the spatial distribution of NADH fluorescence for the test oocyte at the first and the (optional) second times during the early stage of test oocyte meiosis corresponds to the spatial distribution of NADH fluorescence obtained at the first and the (optional) second times for a normal oocyte at the same biological stage as the test oocyte. (See Example 6).

In normal oocytes, mitochondria are distributed in an apparently random fashion at the germinal vesicle ("GV") stage of development. The mitochondria aggregate into small clusters during the germinal vesicle breakdown stage. During oocyte maturation in vitro, the clusters characteristically migrate from the cell periphery to the perinuclear region and form a dense aggregate that surrounds the metaphase I spindle. Subsequent to abstriction of the first polar body, the perinuclear mitochondria disperse. Aberrations in the normal progression of cytoplasmic and mitochondrial maturation have been suspected in early oocyte developmental failure. These aberrations go unnoticed in the standard morphologic assessment of oocytes, and have thus far been identified only after detailed analysis using electron microscopy or potentially toxic fluorescent probes, such as rhodamine 123. (Rhodamine 123 is known to accumulate in mitochondria and inhibit oxidative phosphorylation.) (See Methods in Cell Biology, (1989) eds. Taylor, K. and Wang, Y., Academic Press, Inc., New York, vol. 29, ch. 7 for an extended discussion of rhodamine labeling of mitochondria). In contrast to the prior art methods, the invention provides a non-invasive, non-toxic method for detecting aberrations in the normal progression of oocyte cytoplasmic and mitochondrial maturation.

Example 4 describes the procedures used to demonstrate a correlation between the spatial distributions of NADH fluorescence and rhodamine 123 fluorescence in mouse oocytes. The procedures include comparing the NADH fluorescence and rhodamine 123 fluorescence images (using the Meridian ACAS 570 computer system) and determining the extent of overlap for these images. In view of the observed spatial distribution of NADH fluorescence and rhodamine 123 fluorescence, and further in view of the known correlation between the spatial distribution of rhodamine 123 fluorescence and oocyte maturity, the utility of NADH fluorescence distribution measurements for characterizing the distribution of subcellular mitochondrial aggregates in oocytes and hence, oocyte maturity, has been demonstrated.

A simple, non-invasive method for evaluating membrane integrity and function (and obtaining metabolite transfer rates) is also provided. The method involves: (1) placing the oocyte/embryo in a control medium for a first period of time sufficient to reduce the steady-state NADH concentration; (2) obtaining a control NADH fluorescence measurement; (3) contacting the oocyte/embryo with a nutrient for a second period of time sufficient for the oocyte/embryo to acquire the nutrient; and (4) obtaining at least two post-nutrient NADH fluorescence measurements to obtain a rate of increase of NADH fluorescence following contacting the oocyte/embryo with the nutrient, wherein nutrient utilization is directly proportional to the rate of increase of NADH fluorescence.

Compositions useful for assessing the quality of the oocyte/embryo are also provided. The compositions contain the oocyte/embryo and a modified control medium. As used herein, "modified control medium" refers to a control medium to which has been added some but not all of the essential nutrients required to support normal metabolic activity. Preferably, the modified control medium is a control medium, such as phosphate-buffered saline, to which one or two essential nutrients have been added. (See also Tables 1 and 2 for other preferred modified control media.) In a particularly preferred embodiment, the nutrient is pyruvate and the amount of pyruvate present in the modified control medium is sufficient to support the generation of NADH during the mitochondrial TCA cycle. Other modified control media include phosphate-buffered saline to which glucose or lactate has been added. Optionally, antioxidants are added to the composition.

The following examples further illustrate representative utilities of the above-described methods and compositions for assessing oocyte/embryo quality.

EXAMPLES

INTRODUCTION
Research Design and Methods

NADH fluorescence was measured in an immature and mature mouse oocyte, a one-cell, two-cell, and four-cell mouse embryo, and a mouse blastocyst using an interactive laser-illuminated fluorescence microscope (Meridian ACAS 570) and a temperature-controlled perfusion chamber (Example 1). The objective of utilizing measurement of NADH fluorescence to assess oocyte and embryo quality was accomplished by:

1) establishing the technical feasibility of measuring low-level NADH fluorescence in oocytes, one-cell, two-cell, and four-cell embryos, and blastocysts (Example 2);
2) establishing the safety and non-toxic effect of measuring NADH fluorescence in the oocyte and embryo (Example 3);
3) defining the NADH specificity of the measured fluorescence in the oocyte and embryo (Example 4) by spectroscopic criteria (Example 4a), biochemical criteria (Example 4b), and cell biology criteria (Example 4c);
4) predicting embryo quality (developmental outcome) by the observed change of NADH fluorescence in the nutrient-starved one- to two-cell embryo after the addition of pyruvate nutrient to the culture media (Example 5);
5) detecting aberrations in the normal progression of oocyte cytoplasmic maturation by observing aberrations in the normal peripheral to perinuclear mitochondrial translocation labeled by NADH fluorescence (prophetic Example 6)
6) evaluating the temporal relationship between changes in NADH fluorescence and changes in intracellular free calcium (prophetic Example 7);

7) application of each of the above examples to the human oocyte and embryo (prophetic Example 8).

Each of these experiments is described in detail below.

Special Equipment: The Meridian Instruments ACAS 570 Interactive Laser Cytometer.

The Meridian ACAS 570 is specifically designed for detecting low level fluorescence in living cells. Maximal NADH fluorescence is detected using ultraviolet laser excitation at 351.1–363.8 nm and emission detection at 485 nm (+/–22.5 nm). $NAD^+$ has no inherent fluorescence at these wavelengths. A tunable 15–5000 mWatt argon ion laser is used for excitation; the beam can be controlled with respect to intensity, duration, and spot size. A motorized, computer-interfaced microscope stage automates two dimensional scanning of a sample and permits storage of fluorescence emission data as a function of cell coordinates, allowing comparisons among repeated scans of the same cell over time. Fluorescence can be measured at intervals as small as 0.25 micrometers along the axes of translation of the microscope stage. A sensitive photomultiplier tube captures and digitizes the low level fluorescence signal, and the computer stores the digital fluorescence value with the corresponding stage coordinates. An integrated 80386 computer system provides control of laser intensity and duration, stage movement, photomultiplier tube gain, and data storage, as well as sophisticated data analysis with numeric, graphic, or pseudocolor fluorescence display.

EXAMPLE 1

Design of a temperature-controlled oocyte/embryo perfusion chamber.

Figure 1B:
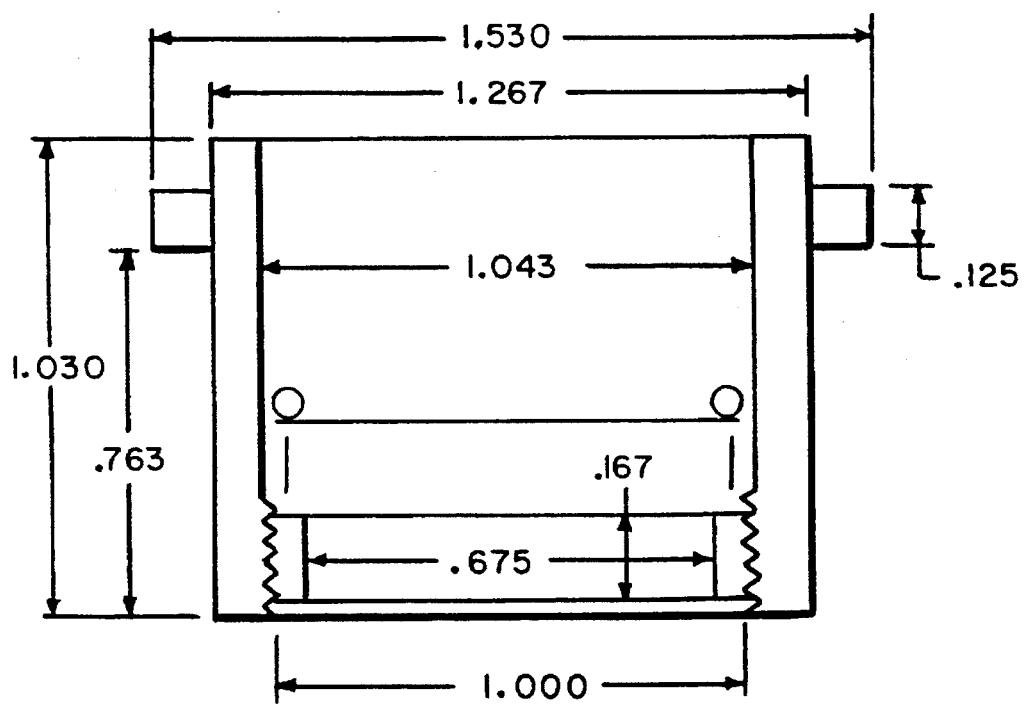

A temperature-controlled oocyte/embryo perfusion chamber,was designed and customized for the Meridian ACAS 570 interactive laser cytometer (FIG. 1). Standard plastic embryo culture dishes do not pass excitation light at ultraviolet wavelengths or permit detection of low level fluorescence emission. The perfusion chamber, with its glass coverslip base, allows the continuous measurement of NADH fluorescence during pulsed perfusion of essential nutrients (e.g., TCA cycle substrates or precursors thereto) or metabolic inhibitors. Temperature control is maintained by a recirculating heated water bath (not shown) and a circumferential brass plate in thermal contact with the sample.

EXAMPLE 2

Establishing the technical feasibility of measuring low-level NADH fluorescence in oocytes, one and two-cell embryos, and blastocysts.

Figure 3:
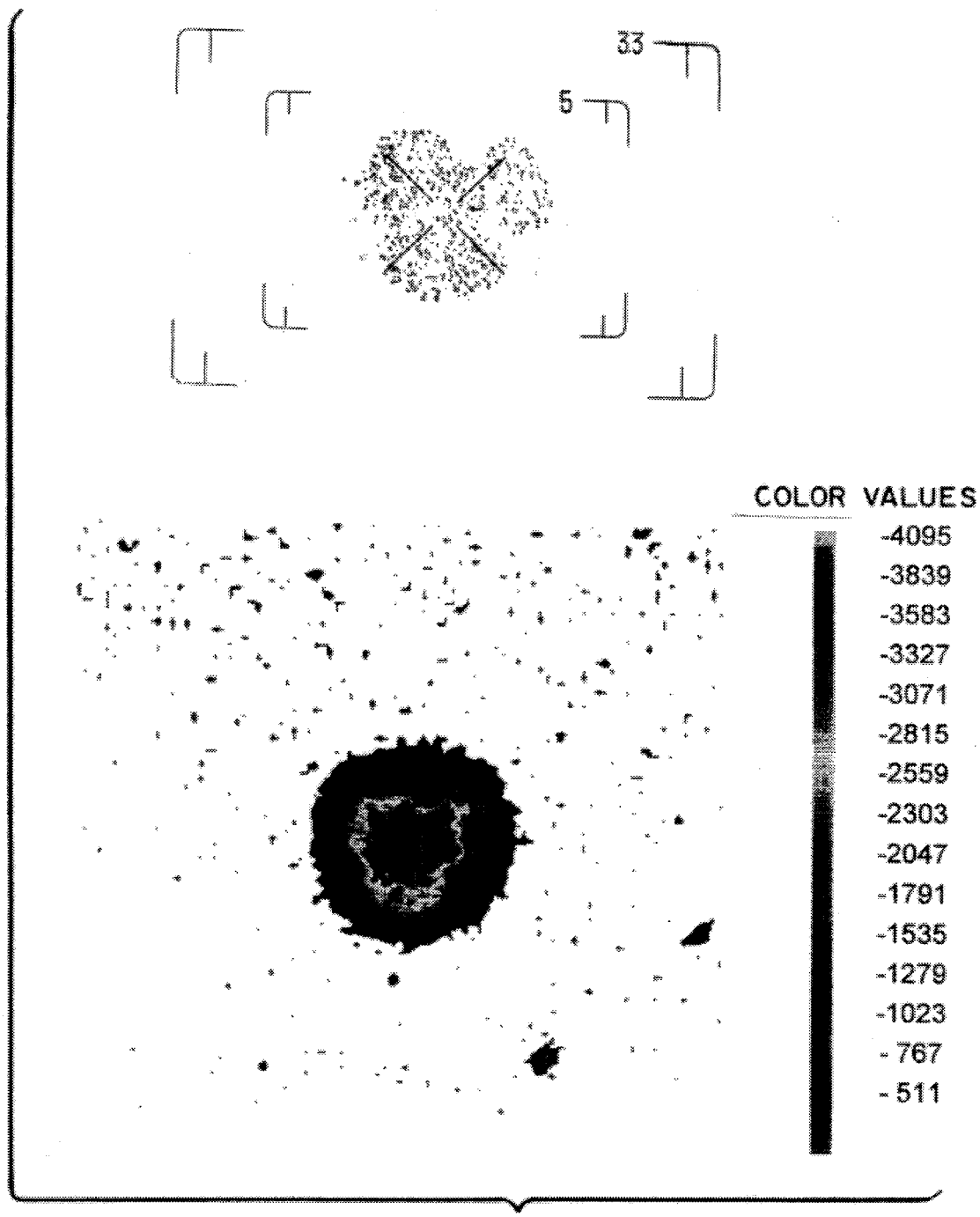
FIG. 3 shows the phase contrast (top) and pseudocolor fluorescence (bottom) images of a four-cell mouse embryo, in which the protrusion of one of the blastomeres along the z-axis is associated with the centrally increased cell mass (phase contrast image) and increased NADH fluorescence (pseudocolor fluorescence image). (Note that FIG. 3 shows concentric areas of increasing fluorescence intensity with a yellow line encircling an intense red center.) The color values ranging from 255 to 4095 indicate the fluorescence intensity. An increase in fluorescence intensity is reflected by a change in the observed color of fluorescence from violet to blue to green to yellow to orange to red at the highest color value.
Figure 4:
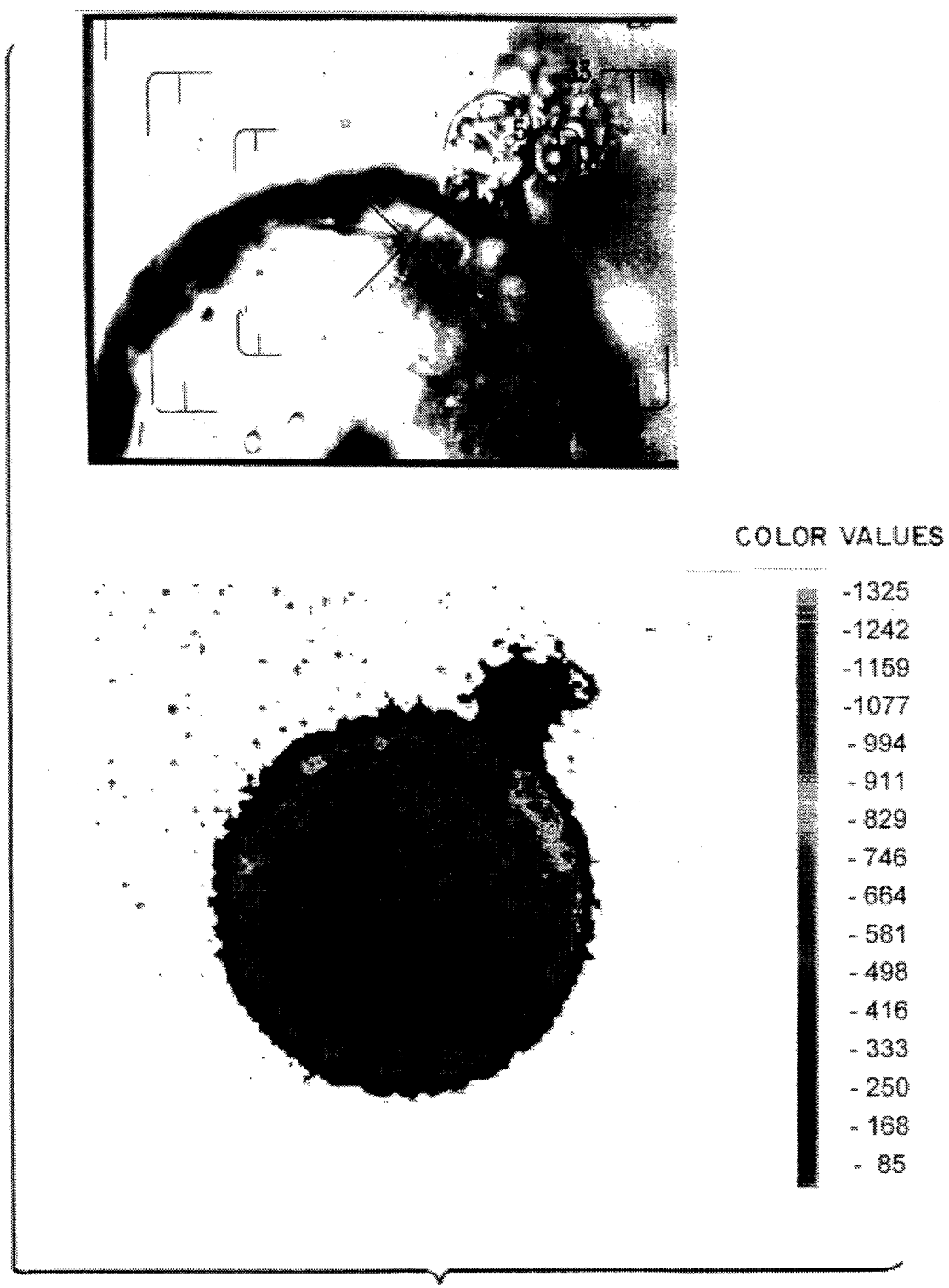
FIG. 4 shows the phase contrast (top) and pseudocolor fluorescence (bottom) images of a hatching mouse blastocyst, in which the NADH fluorescence is concentrated within the inner cell mass and in which the non-cellular blastocyst cavity is appropriately devoid of detectable NADH fluorescence. (Note that FIG. 4 shows areas of yellow and red fluorescence intensity within the inner cell mass and the non-cellular blastocyst cavity lacks detectable NADH fluorescence (shown as violet).) The color values ranging from 255 to 4095 indicate the fluorescence intensity. An increase in fluorescence intensity is reflected by a change in the observed color of fluorescence from violet to blue to green to yellow to orange to red at the highest color value.

The technical feasibility of measuring low-level NADH fluorescence in immature and mature oocytes, one- and two-cell mouse embryos and blastocysts was established by utilizing the Meridian ACAS 570 interactive laser cytometer (FIGS. 2–4). Murine oocytes, one- and two-cell embryos, and blastocysts were obtained from BDF mice in standard fashion after superovulation with 5 IU pregnant mare serum gonadotropin (PMSG). Culture dishes containing growth media with nutrients (Ham's F-10 or KSOM) were equilibrated overnight in an incubator (5% $CO_2$, 5% $O_2$, 90% $N_2$, humidified at 37° C.). Retrieved oocytes, embryos, and blastocysts were rinsed in growth media and individually transferred via micropipette to glass cover slips containing 40 µl drops of growth media covered with embryo-tested mineral oil. Individual glass cover slips containing the oocyte, embryo, or blastocyst were inserted into the perfusion chamber, which was itself placed on the Meridian ACAS 570 microscope stage. Settings on the Meridian ACAS 570 were as follows: UV excitation at 351.1–363.8 nm, band-pass emission filter at 485 nm (+/–22.5 nm) at about 480 nm, argon ion laser power at 200 mW, 15%–20% laser scan strength, 45%–50% photomultiplier tube gain, stage speed at 20 mm/sec, step size 2.00 micrometer. Phase contrast images were recorded using a CCD camera and video printer. Fluorescence images were acquired using the ACAS 570 image scan utility and stored in the ACAS 570 computer. Oocytes, embryos, or blastocysts were thereafter discarded.

In the presence of pyruvate nutrient, all oocytes and embryos tested (n=30) exhibited readily detectable levels of fluorescence emission. Using the 40x and 100x oil immersion microscope objectives, neither the UV laser strength nor the photomultiplier tube gain required maximal settings. Optimal fluorescence detection without photobleaching was obtained at 15%–20% of maximal laser strength and 45%–50% of maximal photomultiplier tube gain.

FIG. 2 (top) depicts a phase contrast image of a germinal vesicle ("GV") stage mouse oocyte with a partially detached cumulus complex. The unique shape of this oocyte-cumulus complex is well represented in the pseudocolor image of measured NADH fluorescence (FIG. 2, bottom). The increased metabolic activity of the compact cumulus is denoted by the higher levels of NADH fluorescence in this region.

FIG. 3 depicts a four-cell mouse embryo. Note that the protrusion of one of the blastomeres along the z-axis is associated with the centrally increased cell mass (FIG. 3, top) and increased NADH fluorescence (FIG. 3, bottom).

FIG. 4 depicts a hatching mouse blastocyst. As would be expected, detectable NADH fluorescence is concentrated within the inner cell mass and is absent from the non-cellular blastocyst cavity.

EXAMPLE 3

Establishing the safety and non-toxic effect of measuring NADH fluorescence in the oocyte and embryo.

Figure 16:
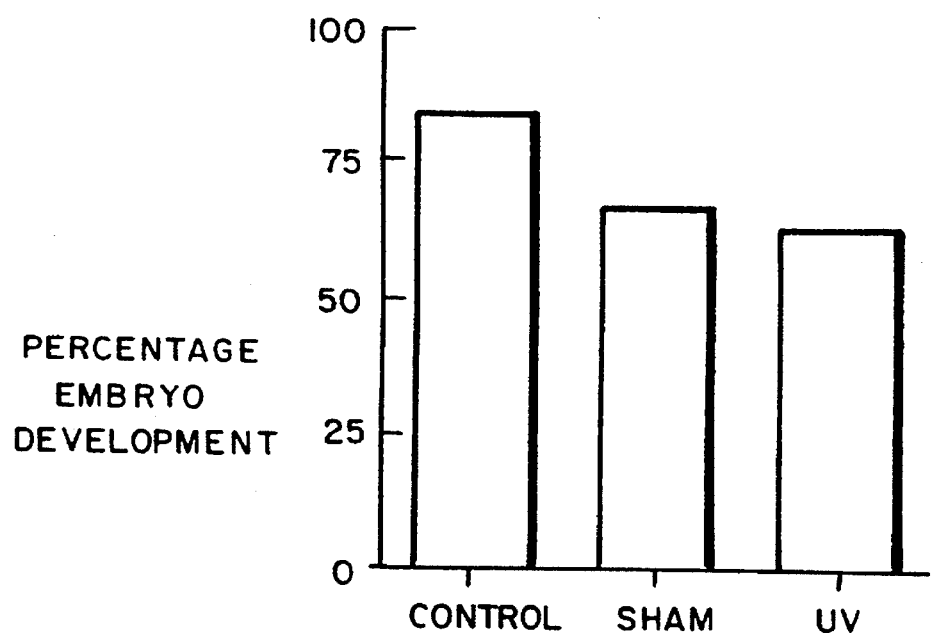
FIG. 16 shows the effect of ultraviolet light on embryo development.

Prolonged ultraviolet excitation may be detrimental to embryo development. Therefore, the effect of transient 351.1–363.8 nm laser excitation by the Meridian ACAS 570 on blastocyst development was measured. Embryos were tested under three different conditions: 1) control group (n=50); 2) sham group (n=50); and 3) UV laser excitation group (n=50). One hundred fifty two-cell murine embryos were retrieved in standard fashion. The control group was subsequently placed in growth media (Ham's F-10) and incubated to blastocyst stage in standard fashion. The sham group of two-cell embryos was transferred individually to 40 µl microdrops of growth media on glass cover slips and mounted on the embryo chamber, as described in Examples 1 and 2. The sham group of embryos was then placed on the stage of the Meridian ACAS 570, with settings as described in Example 2, but the laser was not activated. The UV laser excitation group of two-cell embryos was processed identically to the sham group, except that 351.1–363.8 nm laser excitation was used to scan a fluorescence image of each embryo. Both the sham and UV groups of embryos were subsequently transferred to fresh growth media and cultured in vitro to the blastocyst stage. Outcome of blastocyst development (%) within the three embryo groups is presented in FIG. 16. No significant decrease in blastocyst development was demonstrated between the sham and UV groups, suggesting that transient 351.1–363.8 nm laser excitation was safe and non-toxic to embryo development.

EXAMPLE 4

Defining the NADH specificity of the measured fluorescence in the oocyte and embryo by spectroscopic criteria (Example 4a), biochemical criteria (Example 4b), and cell biology criteria (Example 4c).

EXAMPLE 4a

Spectroscopic criteria.

The excitation spectrum of NADH has two peaks at approximately 260 nm and 340 nm. The fluorescence emission spectrum of NADH has a maximum at about 480 nm and tapers to zero at about 530 nm. The specificity of the disclosed method for detecting NADH fluorescence was demonstrated, in part, by illuminating a one-cell mouse embryo with ultraviolet (351.1–363.8 nm) light from the ACAS 570 argon ion laser and comparing fluorescence emission at 485 nm (+/–22.5 nm) (NADH fluorescence) to that at 530 nm (+/–15 nm) (no NADH fluorescence). NADH fluorescence was detected at 485 nm (+/–22.5 nm). In contrast, the fluorescence was reduced to baseline levels at 530 nm (+/–15 nm) (FIG. 5).

EXAMPLE 4b

Biochemical criteria.

It was necessary to confirm that the fluorescence detected in Example 2 was specifically representative of NADH concentration within the oocyte, embryo, or blastocyst. The NADH specificity of the measured fluorescence was supported by the use of metabolic inhibitors that are known to block specific biochemical pathways and that have known effects on NADH levels. These inhibitors are listed in Table 3.

Figure 10:
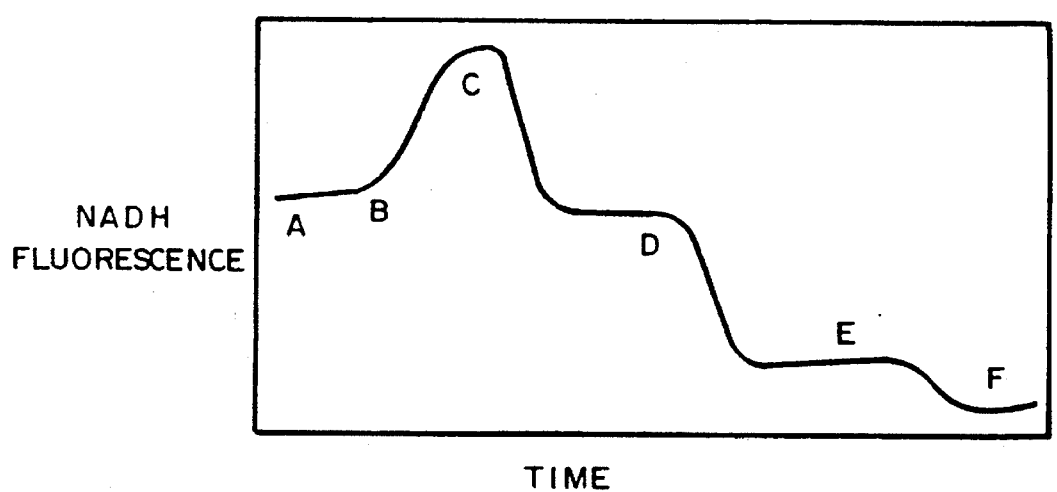
FIG. 10 shows expected changes in NADH relative fluorescence intensity (RFI) in the one- to two-cell embryo after use of metabolic inhibitors. At (A) baseline fluorescence is equilibrated. At (B) the embryo is exposed to 3.3 mM amobarbital to inhibit NADH dehydrogenase; peak NADH fluorescence intensity results. At (C) amobarbital is washed out. At (D) oxidative phosphorylation is uncoupled by perfusion with 0.5 mM FCCP, resulting in minimum NADH fluorescence (E). (F) represents fluorescence from media alone. (C−A)=NADH reserve. (D−E)=NADH generated from oxidative phosphorylation.

FIG. 10 illustrates expected changes in NADH fluorescence in the one- to two-cell embryo after use of the metabolic inhibitors listed in Table 3. At (A) baseline fluorescence is equilibrated. At (B) the embryo is exposed to 3.3 mM amobarbital to inhibit NADH dehydrogenase; peak NADH fluorescence intensity results. At (C) amobarbital is washed out. At (D) oxidative phosphorylation is uncoupled by perfusion with 0.5 mM FCCP, resulting in minimum NADH fluorescence (E). (F) represents fluorescence from media alone. These expected changes were faithfully reproduced in both the one-cell embryo and blastocyst, by using the Meridian ACAS 570 as described in Example 2.

Figure 6:
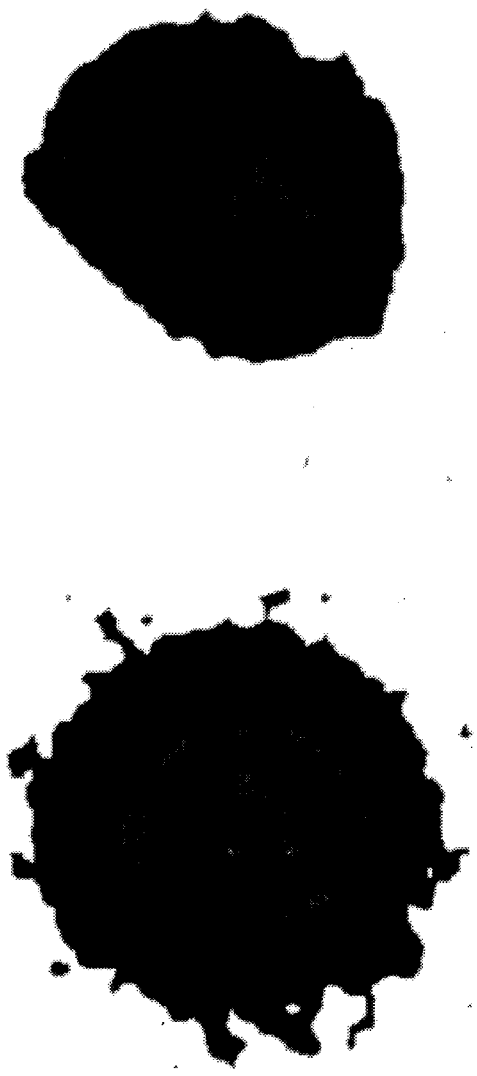
FIG. 6 shows that a pyruvate perfused mouse oocyte exhibits significant NADH fluorescence (left) and that the addition of monofluorocitrate (which blocks the aconitase reaction of the TCA cycle) to the oocyte results in a rapid decrease in measured NADH fluorescence (right). (Note that FIG. 6 shows areas of blue, green and yellow fluorescence intensity for the pyruvate perfused mouse oocyte but that the addition of the inhibitor results in a reduction in NADH fluorescence intensity (shown as violet with a small area of blue).) The color values ranging from 255 to 4095 indicate the fluorescence intensity. An increase in fluorescence intensity is reflected by a change in the observed color of fluorescence from violet to blue to green to yellow to orange to red at the highest color value.

Metabolic inhibitors were tested in both the one-cell embryo and the blastocyst. The concordance between the expected effect on NADH fluorescence and the measured NADH fluorescence fulfilled the biochemical criteria for defining the NADH specificity of the measured fluorescence (Table 3). FIG. 6 demonstrates an example of monofluorocitrate-induced TCA cycle inhibition and the expected decrease in measured NADH fluorescence caused by this inhibitor.

EXAMPLE 4c

Cell biology criteria.

Cell biology criteria were also satisfied as further support for the claim that the measured fluorescence in oocytes and embryos, as described in Example 2, is specific for NADH. NADH is predominantly concentrated within the mitochondria of the oocyte. It was therefore expected that fluorescent labeling of mitochondria (performed using the specific fluorescent probe rhodamine 123) would correspond spatially to the NADH fluorescence detected as described in Example 2.

NADH fluorescence was measured in metaphase II oocytes, as described in Example 2. Pseudocolor fluorescence images were stored for later comparison (see FIG. 8). Thereafter, rhodamine 123 (Sigma Chemicals) was dissolved in distilled water at a concentration of 1 mg/ml, and then diluted in Dulbecco's phosphate buffered saline to a concentration of 10 mg/ml. The metaphase II oocytes were then incubated with the rhodamine 123 solution for 30 minutes in a 5% $CO_2$ incubator at 37° C. Oocytes were rinsed in growth media (Ham's F-10) and transferred to a glass cover slip mounted in the embryo chamber (Example 1). Oocytes were excited in the visual spectrum (514.5 nm) and fluorescence emission measured using a 605 nm long pass filter. The spatial distribution of rhodamine 123 fluorescence corresponded spatially to that of NADH fluorescence in the same oocytes, confirming the mitochondrial localization of the measured NADH fluorescence.

EXAMPLE 5

Predicting embryo quality. (developmental outcome) by the observed change of NADH fluorescence in the nutrient-starved one- to two-cell embryo after the addition of pyruvate nutrient to the culture media.

Figure 7:
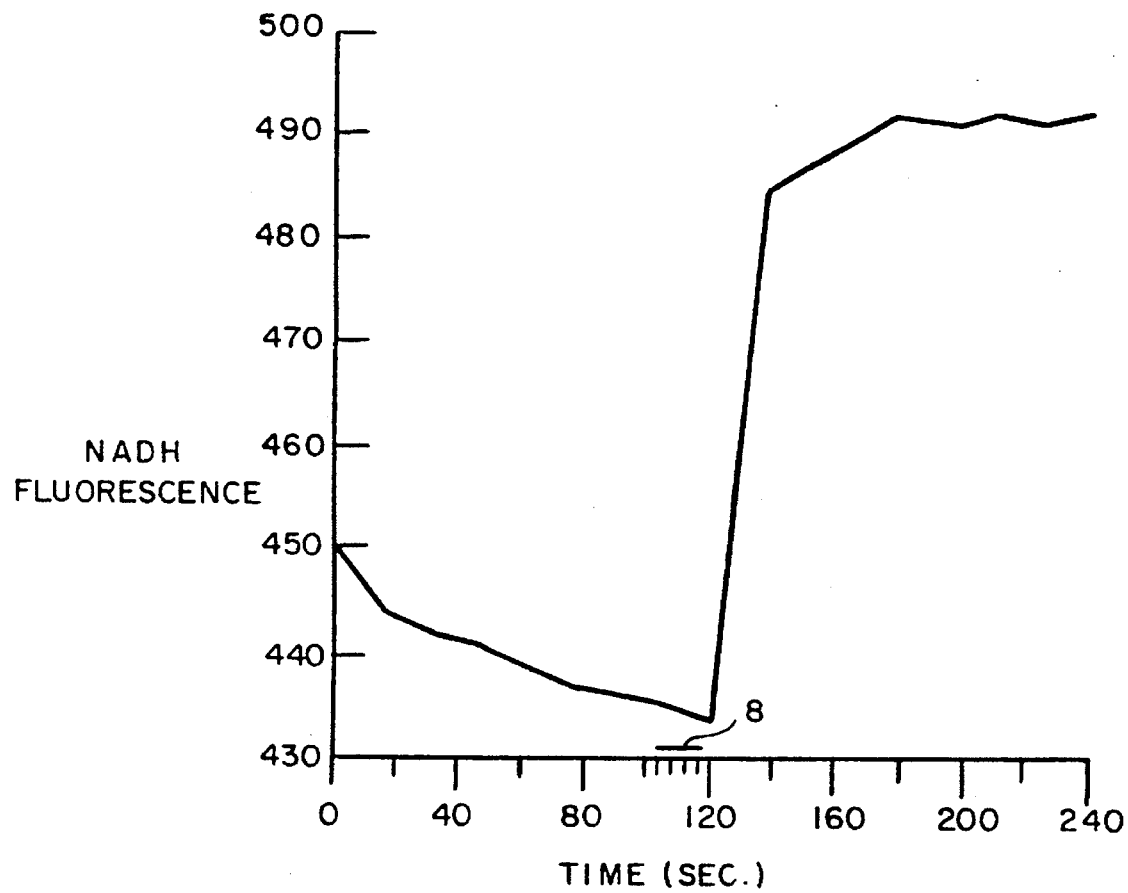
FIG. 7 shows that the addition of pyruvate (at 8) to an immature mouse oocyte that has been nutrient starved by culturing in DPBS at 37 degrees C. for one hour results in a rapid and sustained increase in NADH fluorescence of the oocyte.

Studies were performed that demonstrated a prompt increase in NADH fluorescence following the addition of pyruvate to DPBS starved oocytes (FIG. 7). Similar increases in NADH fluorescence have been correlated with substrate utilization within functional healthy cells (Kohen, E. et al, (1972) (eds: Thaer, A., Sernetz, M.), Springer-Verlag, Berlin, 207–218). It was hypothesized that an increase in NADH fluorescence after pulsed nutrient (pyruvate) contact is predictive of substrate utilization in a functional, high quality oocyte or embryo.

One and two-cell embryos were obtained from BDF mice in standard fashion after PMSG superovulation. Embryos were rinsed and placed in control Dulbecco's phosphate buffered saline (DPBS) for thirty minutes in humidified 5% $CO_2$ at 37° C. After 30 minutes, embryos were transferred using a micropipette to a 40 µl microdrop of DPBS on a glass coverslip mounted in the embryo chamber. Baseline NADH fluorescence was measured using the Meridian ACAS 570, as described in Example 2. Serial measurements (at least 2 measurements with a 15 second delay between scans) were taken to establish a steady-state baseline of measured NADH fluorescence. Those embryos demonstrating steady-state NADH levels were then rapidly transferred to a separate 40 µl microdrop of modified K-SOM pyruvate-rich media, from which glucose and lactate were omitted (Table 2), and immediately placed on a glass coverslip mounted in the embryo chamber. The Meridian ACAS 570 was again used to perform serial measurements (at least 2 measurements with a 15 second delay between scans) of NADH fluorescence. The first NADH fluorescence measurement after embryo contacting with modified K-SOM pyruvate-rich media was designated as time zero, and all subsequent fluorescence measurements were normalized to the time zero value, which was designated as 1.00. This normalization method allowed each embryo to serve as its own control. After completion of the series of NADH measurements, embryos were transferred using a micropipette to Ham's F-10 media and returned to a humidified 5% $CO_2$ incubator at 37° C. Three days later, individually cultured embryos were assessed for blastocyst development.

Upon addition of pyruvate to the nutrient-starved embryos, three distinct patterns of serial NADH fluorescence measurements were noted: 1) a progressive increase in NADH fluorescence (n=22) (FIG. 11); 2) no change in NADH fluorescence (n=8) (FIG. 14); or 3) a progressive decrease in NADH fluorescence (n=14) (FIGS. 12 and 13).

Figure 15:
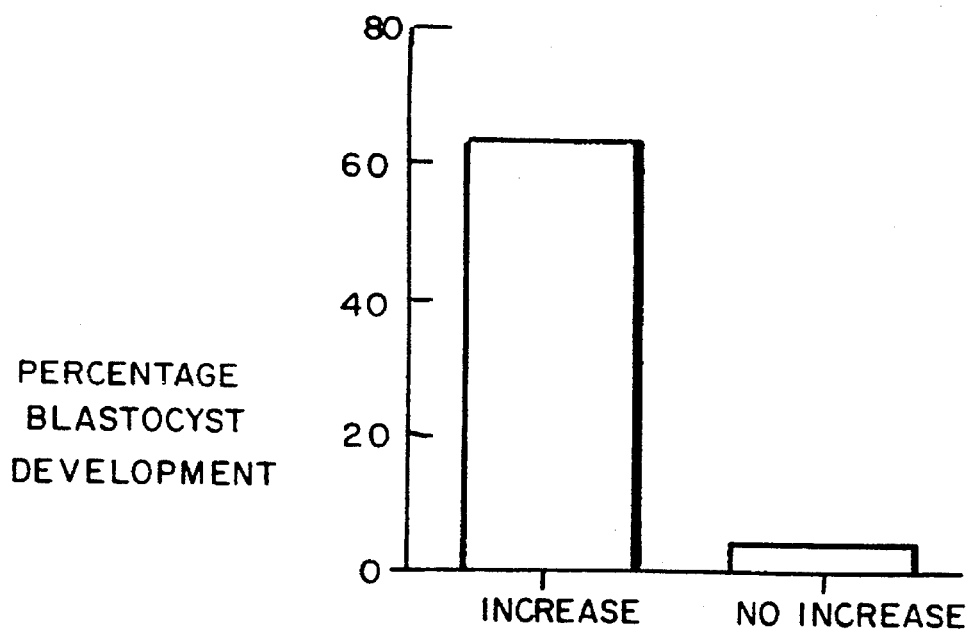
FIG. 15 shows the rate of successful development of 1–2 cell embryos to the blastocyst stage as a function of the NADH fluorescence response to pyruvate (nutrient) contact.

When the embryos were grouped according to the absence (n=22) or presence (n=22) of an increase in NADH fluorescence, a significantly greater percentage of those embryos demonstrating increased NADH fluorescence over time went on to normal blastocyst development (64% for the group demonstrating increased NADH fluorescence over time versus 5% for the group demonstrating no change or decreased NADH fluorescence over time; FIG. 15). These results demonstrated the potential value of NADH fluorescence measurements as predictive of blastocyst development and embryo quality.

EXAMPLE 6

Detecting aberrations in the normal progression of oocyte cytoplasmic maturation by observing aberrations in the normal peripheral to perinuclear mitochondrial translocation labeled by NADH fluorescence.

Van Blerkom et al (1991, Proc. Natl. Acad. Sci. U.S.A. 88, 5031–5) correlated changes in the spatial distribution of mitochondria with cytoplasmic maturation during the early stages of resumed meiosis in murine, bovine, and human oocytes after exogenous ovarian hyperstimulation. During oocyte maturation in vitro, clusters of mitochondria characteristically migrate to the perinuclear region and form a dense aggregate that surrounds the metaphase I spindle (see FIG. 8). Aberrations in the normal progression of cytoplasmic maturation have been suspected in early oocyte developmental failure. These aberrations go unnoticed in the standard morphologic oocyte assessment, and have thus far been identified only after detailed analysis using electron microscopy or potentially toxic fluorescent probes, such as rhodamine 123 (which is known to accumulate in mitochondria and inhibit oxidative phosphorylation).

Measurements of mitochondrial NADH fluorescence (see Example 4c) are performed in the following groups, each containing 20 oocytes: 1) mouse GV stage oocytes at time 0 (30 minutes after collection), 1 hour, and 3 hours; 2) mouse and GV stage oocytes in culture medium containing 5 mM 3-isobutyl-1-methylxanthine (IBMX) to inhibit meiotic resumption at time 0 (30 minutes after collection), 1 hour, and 3 hours (Inhibiting meiotic resumption prevents the normal mitochondrial translocation and serves as a negative control.); 3) mature (GVBD) stage mouse oocytes at time 0 (30 minutes after collection). All mouse oocytes are fertilized in vitro after GVBD (maturation), and development to two-cell and blastocyst stages is documented. Correlation is determined between oocytes demonstrating normal mitochondrial translocation and subsequent development to the blastocyst stage.

EXAMPLE 7

Evaluating the temporal relationship between changes in NADH fluorescence and changes in intracellular free calcium.

In 1964, using a simple fluorimeter, Epel reported a rapid increase in NADH fluorescence associated with fertilization of the sea urchin egg, and concluded that the metabolic role of NADH is of fundamental importance in egg activation (Epel, D., (1964) Biochem. Biophys. Res. Commun. 17(1), 62–68). It has since been demonstrated that fertilization is associated with a large rise in intracellular free calcium ($[Ca^{2+}]_i$) (Jaffe, L., (1983) Dev. Biol. 99, 265–276). In mouse and human oocytes, the spermatozoon triggers a series of $Ca^{2+}$ oscillations that recur for several hours (Homa, S. et al, (1993) Human Reprod. 8(8), 1274–1281). A separate role for $Ca^{2+}$ in triggering meiotic resumption and progression to metaphase II in the oocyte has been proposed but is less clearly defined. Calcium oscillations, in which cytosolic $Ca^{2+}$ is derived from intracellular $Ca^{2+}$ stores, have been observed over the first few hours of meiotic resumption (Carroll, J. et al, (1992) J. Biol. Chem. 267, 11196–201).

Calcium ions are released from both mitochondrial and microsomal stores. Mitochondrial uncouplers such as FCCP collapse the mitochondrial membrane potential, resulting in $Ca^{2+}$ release, and can therefore be used to estimate mitochondrial $Ca^{2+}$ stores (Murphy, E. et al, (1980) J. Biol. Chem. 255, 6600–6608). The release of $Ca^{2+}$ by mitochondria is dependent on metabolic redox states ($NADH/NAD^+$) (Livingston, F. et al, (1992) Archiv. Biochem. Biophysics 299(1), 83–91). In a different cellular system, Pralong et al examined the changes in NADH fluorescence and $[Ca^{2+}]_i$ following stimulation of single pancreatic beta-cells with glucose (Pralong, W. et al, (1990) EMBO J. 9(1), 53–60). In healthy cells, the elevation of NADH fluorescence consistently preceded the rise in $[Ca^{2+}]_i$. It is of interest, therefore, to define the relationship between measured NADH fluorescence and $[Ca^{2+}]_i$ in both the developing oocyte and upon fertilization, and to determine if changes in NADH fluorescence are predictive of $[Ca^{2+}]_i$ fluctuations. This relationship will assume increasing clinical importance with the increased use of intracytoplasmic sperm injection and its associated effect on calcium release (Edwards, R., (1993) Hum. Reprod. 8(7), 988–989).

The purpose of the Example is to define the temporal relationship between changes in NADH fluorescence and $[Ca^{2+}]_i$, and not to define or redefine the role of $[Ca^{2+}]_i$ in oocyte maturation. If a reproducible, coordinated increase is found in both NADH fluorescence and $[Ca^{2+}]_i$, NADH fluorescence alone could serve as a non-invasive, indirect assessment of $[Ca^{2+}]_i$ in the oocyte or embryo.

Oocytes are loaded for 20 minutes at 37° C. in the presence of 0.5 mM fluo-3 (Molecular Probes). The ACAS 570 is modified to incorporate a Coherent Enterprise argon ion laser capable of simultaneous light output at UV (351.1–363.8 nm) and visible (488 nm or 514.5 nm) wavelengths. UV light is used to excite NADH fluorescence, and 488 nm light is used to excite fluo-3 fluorescence. Fluorescence emission is simultaneously measured at about 470 nm (NADH) and about 520 nm ($[Ca^{2+}]_i$). As both a positive control for $[Ca^{2+}]_i$ and negative control for NADH, FCCP (0.5 mM) is added to isolated oocyte and embryo systems. FCCP collapses the mitochondrial membrane potential, resulting in $Ca^{2+}$ release and marked decrease in NADH fluorescence.

Simultaneous measurements of NADH and $[Ca^{2+}]_i$ are performed on metaphase II oocytes just prior to and during fertilization. Frequency of measurements is adjusted so as-to best document the oscillatory pattern of $Ca^{2+}$ release.

EXAMPLE 8

Application of each of the above examples to the human oocyte and embryo.

All of the above examples are carried out in the mouse model. Current experimental research in the human system is limited to study of the unfertilized oocyte. Examples 2 through 7 are reproduced using the human unfertilized oocyte. With the advent of increased human embryo research, Examples 2 through 7 are reproduced using the human embryo. It should be apparent to those skilled in the an that various modifications and equivalents may be required in order to reproduce Examples 2 through 7 using human oocytes/embryos, without departing from the spirit or scope of the invention.

Each of the above-identified references is incorporated in its entirety herein by reference. It should be further understood that the preceding is merely a detailed description of certain preferred embodiments. It therefore should be apparent to those skilled in the art that various modifications and equivalents can be made without departing from the spirit or scope of the invention.

What is claimed is:

1. A method for assessing the quality of a pre-implantation embryo for implantation, the embryo having a steady-state NADH concentration, the method comprising:

(1) placing the embryo in a control medium for a first period of time sufficient to reduce the steady-state NADH concentration, wherein the control medium is lacking an essential nutrient selected from the group consisting of pyruvate, glucose and lactate;

(2) measuring NADH fluorescence within the embryo to obtain a control NADH measurement;

(3) contacting the embryo with the lacking essential nutrient for a second period of time sufficient for the embryo to acquire the nutrient;

(4) measuring NADH fluorescence within the embryo to obtain a post-nutrient NADH fluorescence measurement;

(5) comparing the control NADH fluorescence measurement to the post-nutrient NADH fluorescence measurement, wherein the quality of the embryo for implantation is higher when the post-nutrient NADH fluorescence measurement is greater than the control NADH fluorescence measurement.

2. The method of claim 1, wherein at least two post-nutrient NADH fluorescence measurements of NADH fluorescence within the embryo are obtained.

3. The method of claim 2, wherein the quality of the embryo is higher when the post-nutrient NADH fluorescence measurements increase with time following contacting the embryo with the nutrient.

4. The method of claim 2, further comprising normalizing the control NADH fluorescence measurement to 1.0 and wherein the post-nutrient NADH fluorescence measurements are obtained at 0, 60, and 120 seconds after contacting the embryo with the nutrient.

5. The method of claim 2, wherein the pre-implantation embryo comprises a human embryo.

6. The method of claim 2, wherein the pre-implantation embryo comprises a murine embryo.

7. The method of claim 1, wherein the control medium is selected from the group consisting of phosphate buffered saline, modified Potassium Simplex Optimization Media control medium and CZB control medium.

8. The method of claim 1, wherein the first period of time is less than thirty minutes.

9. The method of claim 8, wherein the first period of time is less than fifteen minutes.

10. The method of claim 1, wherein obtaining the control NADH measurement comprises illuminating the embryo with light having a wavelength of about 350 nm and measuring the NADH fluorescence at about 485 nm.

11. The method of claim 10, wherein illuminating comprises illuminating with ultraviolet light from an argon ion laser.

12. The method of claim 1, wherein contacting the embryo with the nutrient is for at least thirty seconds.

13. The method of claim 1, wherein contacting the embryo with the nutrient is for at least 120 seconds.

14. The method of claim 1, wherein the nutrient comprises pyruvate.

15. The method of claim 1, wherein obtaining the post-nutrient NADH measurement comprises illuminating the embryo with light having a wavelength of about 350 nm and measuring the NADH fluorescence at about 485 nm.

16. The method of claim 15, wherein illuminating comprises illuminating with ultraviolet light from an argon ion laser.

17. A method for assessing the quality of an oocyte for in vitro fertilization and implantation, the oocyte having a steady-state NADH concentration, the method comprising:

(1) placing the oocyte in a control medium for a first period of time sufficient to reduce the steady-state NADH concentration, wherein the control medium is lacking an essential nutrient selected from the group consisting of pyruvate, glucose and lactate;

(2) measuring NADH fluorescence within the oocyte to obtain a control NADH measurement;

(3) contacting the oocyte with the locking essential nutrient for a second period of time sufficient for the oocyte to acquire the nutrient;

(4) measuring NADH fluorescence within the oocyte to obtain a post-nutrient NADH fluorescence measurement; and (5) comparing the control NADH fluorescence measurement to the post-nutrient NADH fluorescence measurement, wherein the quality of the oocyte for in vitro fertilization and implantation is higher when the post-nutrient NADH fluorescence measurement is greater than the control NADH fluorescence measurement.

18. A method for detecting an aberration in the normal progression of cytoplasmic maturation for a test oocyte at an early stage of oocyte meiosis, the test oocyte having a steady-state NADH concentration, the method comprising:

obtaining a first fluorescence measurement showing a spatial distribution of NADH fluorescence within the test oocyte at a first time during the early stage of oocyte meiosis; and detecting the aberration in the normal progression of cytoplasmic maturation for the test oocyte by determining whether the spatial distribution of NADH fluorescence within the test oocyte at the first time during the early stage of oocyte meiosis corresponds to the spatial distribution of NADH fluorescence within a normal oocyte that is obtained at the first time for the normal oocyte at the same early stage of oocyte meiosis as the test oocyte, wherein a lack of correspondence between the spatial distribution of NADH fluorescence within the test oocyte and the spatial distribution of NADH fluorescence within the normal oocyte is indicative of an aberration in the normal progression of cytoplasmic maturation for the test oocyte.

19. The method of claim 18, further comprising the step of obtaining a second fluorescence measurement of NADH fluorescence within the test oocyte showing the spatial distribution of NADH fluorescence at a second time during the early stage of oocyte meiosis; and determining whether the spatial distribution of NADH fluorescence within the test oocyte at the first and the second times during the early stage of oocyte meiosis corresponds to the spatial distribution of NADH fluorescence within a normal oocyte that is obtained at the first and the second times for the normal oocyte at the same early stage of meiosis as the test oocyte.

20. A method for assessing nutrient utilization by an embryo having a steady-state NADH concentration, the method comprising:

(1) placing the embryo in a control medium for a first period of time sufficient to reduce the steady-state NADH concentration, wherein the control medium is lacking an essential nutrient selected from the group consisting of pyruvate, glucose and lactate;

(2) measuring NADH fluorescence within the embryo to obtain a control NADH measurement;

(3) contacting the embryo with the lacking essential nutrient for a second period of time sufficient for the embryo to acquire the nutrient; and (4) measuring NADH fluorescence within the embryo at least twice to obtain at least two post-nutrient NADH fluorescence measurements within the embryo to obtain a rate of increase of NADH fluorescence following contacting the embryo with the lacking essential nutrient, wherein nutrient utilization is directly proportional to the rate of increase of NADH fluorescence.

* * * * *